US006172026B1

(12) United States Patent
Ospinal et al.

(10) Patent No.: US 6,172,026 B1
(45) **Date of Patent: *Jan. 9, 2001**

(54) SOAP BAR COMPOSITIONS COMPRISING ALPHA SULFONATED FATTY ACID ALKYL ESTERS AND LONG CHAIN FATTY ACIDS

(75) Inventors: Carlos E. Ospinal, Palatine; Jeffrey S. Nelson, Lake Bluff; Catherine J. Sporer, Lindenhurst, all of IL (US); Marshall J. Nepras, Burlington, WI (US)

(73) Assignee: Stepan Company, Northfield, IL (US)

( * ) Notice: Under 35 U.S.C. 154(b), the term of this patent shall be extended for 0 days.

This patent is subject to a terminal disclaimer.

(21) Appl. No.: 09/368,966

(22) Filed: Aug. 5, 1999

Related U.S. Application Data

(63) Continuation of application No. 08/955,845, filed on Oct. 21, 1997, now Pat. No. 5,965,508.

(51) Int. Cl.[7] .......................... C11D 17/00; C11D 15/00; A61K 7/50

(52) U.S. Cl. .......................... 510/355; 510/152; 510/154; 510/353; 510/354; 510/445; 510/446; 510/447; 510/448; 510/489; 510/491; 510/495

(58) Field of Search .................................... 510/130, 152, 510/153, 154, 353, 354, 355, 445, 446, 447, 448, 495, 491, 489

(56) References Cited

U.S. PATENT DOCUMENTS

| | | |
|---|---|---|
| 2,303,212 | 11/1942 | Kise et al. . |
| 2,678,921 | 5/1954 | Turek, Jr. . |
| 2,867,586 | 1/1959 | Weil et al. . |
| 3,223,645 | 12/1965 | Kalberg . |
| 3,247,121 | 4/1966 | Hendricks . |
| 3,274,117 | 9/1966 | Stein et al. . |
| 3,915,903 | 10/1975 | Wise . |
| 4,133,779 | 1/1979 | Hellyer et al. . |
| 4,316,824 | 2/1982 | Pancheri . |
| 4,404,143 | 9/1983 | Sekiguchi et al. . |
| 4,435,317 | 3/1984 | Gerritsen et al. . |
| 4,438,025 | 3/1984 | Satsuki et al. . |
| 4,495,092 | 1/1985 | Schmid et al. . |
| 4,668,438 | 5/1987 | Pierr et al. . |
| 4,681,704 | 7/1987 | Bernardino et al. . |

(List continued on next page.)

FOREIGN PATENT DOCUMENTS

| | | |
|---|---|---|
| 949843 | 6/1974 | (CA) . |
| 2052881 | 5/1972 | (DE) . |
| 2403895 | 1/1974 | (DE) . |
| 2333356 | 1/1975 | (DE) . |
| 2416745 | 6/1975 | (DE) . |
| 2804324 | 8/1978 | (DE) . |
| 3913385 | 10/1990 | (DE) . |
| 40 09 096 | 9/1991 | (DE) . |
| 0 039 110 | 11/1981 | (EP) . |
| 0 254 653 | 1/1988 | (EP) . |
| 0 281 028 | 9/1988 | (EP) . |
| 0 530 708 | 3/1993 | (EP) . |
| 2 118 560 | 7/1972 | (FR) . |
| 2 316 324 | 1/1977 | (FR) . |
| 2 316 325 | 1/1977 | (FR) . |
| 2 462 474 | 2/1981 | (FR) . |
| 2179055 | 2/1987 | (GB) . |
| 50-151905 | 12/1975 | (JP) . |
| 51-47007 | 4/1976 | (JP) . |
| 52-28507 | 3/1977 | (JP) . |

(List continued on next page.)

OTHER PUBLICATIONS

R. G. Bistline et al., "Soap–Based Detergent Formulations I. Comparison of Soap—Lime Soap Dispersing Agent Formulations With Phosphate Built Detergents," *J. Am. Oil Chem. Soc.*, vol. 49, pp. 63–69, Jan. 1972.

D. Desai et al., "Soap/Alpha–Sulfo Methyl Ester Based Liquid Laundry Detergents," *Research Disclosure*, 30605, Oct. 1989.

J.C. Drozd, "Use of Sulfonated Methyl Esters In Household Cleaning Products," *Proc. World Conf. Oleochem.*, pp. 256–268, 1991.

J.C. Drozd et al., "Liquid Laundry Detergents Based on Soap and α–Sulfo Methyl Esters," *J. Am. Oil Chem. Soc.*, vol. 68, No. 1, pp. 59–62, Jan. 1991.

E. A. Knaggs et al., "Alpha Sulfo Fatty Esters in Biologically Soft Detergent Formulations," *J. Am. Oil Chem. Soc.*, vol. 42, pp. 805–810, 1965.

E. W. Maurer et al., "Biological Behavior of Some Soap–Based Detergents," *J. Am. Oil Chem. Soc.*, vol. 51, pp. 287–291, Jul. 1974.

T. Satsuki et al., "Performance and Physicochemical Properties of α–Sulfo Fatty Acid Methyl Esters," *J. Am. Oil Chem. Soc.*, vol. 69, No. 7, pp. 672–677, Jul. 1992.

(List continued on next page.)

* cited by examiner

*Primary Examiner*—Yogendra Gupta
*Assistant Examiner*—Gregory E. Webb
(74) *Attorney, Agent, or Firm*—McDonnell Boehnen Hulbert & Berghoff

(57) ABSTRACT

Disclosed are compositions suitable for formation into mild personal cleansing or laundry detergent bars, as well as other uses. The compositions generally comprise:

(a) from about 30% to about 99% by weight of a mixture of anionic surfactants comprising:
  i) an alpha sulfonated alkyl ester; and
  ii) a sulfonated fatty acid;

(a) from about 0.5% to about 50% by weight of a fatty acid; and (b) from about 0.1% to about 50% by weight water;

wherein the ratio of i) to ii) is from about 10:1 to about 0.5:1, and wherein the ratio of (a) to (b) is about 1:1 to about 11:1.

10 Claims, No Drawings

U.S. PATENT DOCUMENTS

| | | | |
|---|---|---|---|
| 4,772,425 | 9/1988 | Chirash et al. . | |
| 4,772,426 | 9/1988 | Koch et al. . | |
| 5,200,115 | 4/1993 | Giesen et al. . | |
| 5,225,097 | 7/1993 | Kacher et al. . | |
| 5,328,632 | 7/1994 | Redd et al. . | |
| 5,393,449 | 2/1995 | Jordan et al. . | |
| 5,409,640 | 4/1995 | Giret et al. . | |
| 5,429,773 | 7/1995 | Sherry et al. . | |
| 5,454,981 | 10/1995 | Sherry et al. . | |
| 5,454,982 * | 10/1995 | Murch et al. | 252/548 |
| 5,494,612 | 2/1996 | Finucane . | |
| 5,510,050 | 4/1996 | Dunbar et al. . | |
| 5,527,489 | 6/1996 | Tadsen et al. . | |
| 5,540,852 | 7/1996 | Kefauver et al. . | |
| 5,607,910 | 3/1997 | Sherry et al. . | |
| 5,616,781 | 4/1997 | Sajic et al. . | |
| 5,965,508 | 10/1999 | Ospinal et al. . | |
| 5,994,281 | 11/1999 | He et al. . | |

FOREIGN PATENT DOCUMENTS

| | | |
|---|---|---|
| 53-27603 | 3/1978 | (JP) . |
| 53-29314 | 3/1978 | (JP) . |
| 55-108496 | 8/1980 | (JP) . |
| 58-80394 | 5/1983 | (JP) . |
| 58-80395 | 5/1983 | (JP) . |
| 58-80396 | 5/1983 | (JP) . |
| 59-4697 | 1/1984 | (JP) . |
| 59-4699 | 1/1984 | (JP) . |
| 59-59797 | 4/1984 | (JP) . |
| 59-221392 | 12/1984 | (JP) . |
| 59-221394 | 12/1984 | (JP) . |
| 59-221395 | 12/1984 | (JP) . |
| 59-221399 | 12/1984 | (JP) . |
| 62-43500 | 2/1987 | (JP) . |
| 62-115096 | 5/1987 | (JP) . |
| 4-202300 | 7/1992 | (JP) . |
| 4-213399 | 8/1992 | (JP) . |
| 8-302398 | 11/1996 | (JP) . |
| 23 687 | 9/1989 | (PH) . |
| WO 92/06156 | 4/1992 | (WO) . |
| WO 92/06157 | 4/1992 | (WO) . |
| WO 94/26866 | 11/1994 | (WO) . |
| WO 95/27036 | 10/1995 | (WO) . |
| WO 95/27037 | 10/1995 | (WO) . |
| WO 95/27038 | 10/1995 | (WO) . |
| WO 97/43396 | 11/1997 | (WO) . |
| WO 98/30193 | 7/1998 | (WO) . |
| WO 99/42554 | 8/1999 | (WO) . |

OTHER PUBLICATIONS

F. Schambil et al., "Physico–Chemical Properties of α–Sulpho Fatty Acid Methyl Esters and α–Sulpho Fatty Acid DiSalts," *Physical Chemistry*, Carl Hanser Verlag, 1990.

N. R. Smith, "Alpha–Sulfo Methyl Esters a New Alternative," *Soap/Cosmetics/Chemical Specialties*, pp. 48–57 and 130–136, Apr. 1989.

A. J. Stirton, "α–Sulfo Fatty Acids and Derivatives: Synthesis, Properties and Use," *J. Am. Oil Chem. Soc.*, vol. 39, pp. 490–496, Nov. 1962.

J. K. Weil et al., "Surface Active Properties of Combinations of Soap and Lime Soap Dispersing Agents," *J. Am. Oil Chem. Soc.*, vol. 54, pp. 339–346, 1976.

J. K. Weil et al., "The Mutual Solubilization of Soap and Lime Soap Dispersing Agents," *J. Am. Oil Chem. Soc.*, vol. 54, pp. 1–3, 1977.

SOAP BAR COMPOSITIONS COMPRISING ALPHA SULFONATED FATTY ACID ALKYL ESTERS AND LONG CHAIN FATTY ACIDS

This application is a continuation of Ser. No. 08/955,845 filed Oct. 21, 1997 now U.S. Pat. No. 5,965,508.

BACKGROUND OF THE INVENTION

1. Field of the Invention

The present invention relates to compositions suitable for formation into mild personal cleansing and/or laundry detergent bars. More specifically, it relates to liquid, paste, and flaked compositions suitable for processing into solid or semi-solid suitable for formation into mild personal cleansing and/or laundry detergent bars. Additionally, the compositions are suitable for use in formulated laundry and dish cleaning pastes or gels.

2. Description of the Related Art

Mild personal cleansing and laundry cleaning bar preparations have become a focus of great interest. People wash and exfoliate their skin with various surface-active detergent bar formulations several times a day. Ideal skin cleanser bars should cleanse the skin gently, causing little or no irritation, without defatting and over-drying the skin or leaving it taut after frequent routine use. Most lathering soap bars fail in this respect.

The processability of such bars and their precursor detergent compositions has also become a focus of great interest. The mildness, processability, firmness and smear properties of such bars have become a focus of even greater interest.

Synthetic detergent bars, frequently called "combo bars" (e.g., having substantial amounts of soap) and/or "syndet bars" (e.g., having very little or no soap) are well known to the art, along with natural "soap" bars for personal care use. Syndet bars often possess poor physical properties, e.g., off odors, poor processability, stickiness, brittleness, bar messiness, lather quality, lack of mildness or combinations thereof. Additionally, the problems of formulating synthetic detergent bars are not limited to the performance characteristics of the finished bars. Most bars which are made with certain mild surfactants are very difficult to fabricate.

In contrast, the fabrication of relatively pure "soap" bars is a well-worked-out engineering procedure involving milling, plodding and molding. For example, coco/tallow soap becomes quite plastic when warmed and can be easily plodded and molded under relatively low pressures. However, most synthetic detergents and detergent-filler compositions for use in cleansing or laundry detergent bars do not become plastic and the machinery for fabrication must be specially designed. See U.S. Pat. No. 2,678,921, J. A. V. Turck, Jr., issued May 18, 1954.

Ideal processing of syndet bars or synthetic detergent bars should be fast and problem free in terms of milling, plodding and molding toilet bar formations. Most mild syndet bar processings fall short in some or all of these respects.

Synthetic detergent bar formulations for personal care use are well known to the art. For example, see U.S. Pat. 5,328,632, Redd, et al., issued Jul. 12, 1994; U.S. Pat. 5,510,050, Dunbar, et al., issued Apr. 23, 1996; U.S. Pat. No. 5,393,449, Jordan, et al., issued Feb. 28, 1995; WO 95/27036, Fakoukakis, et al., filed Mar. 30, 1995; and WO 95/27038, Faoukakis, et al., filed Mar. 30, 1995.

Major drawbacks of most synthetic surfactant toilet bar formulations are harshness, poor lather, poor smear, and poor processability due to stickiness. The use of high sudsing anionic surfactants can yield acceptable lather volume. Unfortunately, the highest sudsing anionic surfactants are, in fact, poor in processability. While some prior art mild blends of sodium coconut/tallow alkyl glyceryl ether sulfonate (AGS) are relatively good in lather potential, they are difficult to process because of their stickiness or hygroscopicity. It will be appreciated that processability, firmness, smear, mildness, lather, and rinsability make surfactant selection and stoicheometry for mild personal cleansing bars a critical and difficult task. Thus, it will be appreciated that rather stringent requirements for formulating mild personal cleansing bars limit the choice of surfactants, and final formulations represent some degree of compromise. Mildness is often obtained at the expense of processability, effective cleansing, lathering, or rinsing, or vice versa. Processability is often obtained at the expense of smear.

Synthetic detergent bar formulations for laundry cleaning are also well known to the art. For example, see WO 95/27036, Fakoukakis, et al., filed Mar. 30, 1995; and WO 95/27038, Faoukakis, et al., filed Mar. 30, 1995. Such laundry detergent bars have found expanded use in regions of the world where automatic clothes washing machines are not common. The ideal laundry detergent bar is effective in cleaning clothes, has acceptable sudsing characteristics, has low smear, and pleasing odor and appearance. As these laundry detergent bars are in contact with the skin during clothes washing, mildness is also highly desirable.

Methods for making laundry detergent bars are well known in the art. For example, see Philippine Pat. No. 23,689, issued Sep. 27, 1989 to Unilever; and Philippine Pat. No. 24,551, issued Aug. 3, 1990 to Unilever. Much like the syndet bars for personal care use, laundry detergent bars often possess the same physical problems, e.g., harshness, poor lather, poor smear, and poor processability due to stickiness.

Thus, a need exists for superior processable, mild personal cleansing and/or laundry detergent bar formulations with good mildness, processability, smear, lather potential and rinsability.

Accordingly, a key aspect of the present invention is the surprising synergy present between an alpha sulfonated alkyl ester and an sulfonated fatty acid. The properties of mono and di salt forms of sulfonated fatty acids (i.e. an alpha sulfonated alkyl ester and a sulfonated fatty acid) have been studied and reported by Stirton (see Stirton, A. J. JAOCS 39, 490–496 "Alpha Sulfo Fatty Acids and Derivatives: Synthesis, Properties and Use"), wherein sulfonated fatty acid disalts (pelargonate, laurate, and myristate) are primarily simple electrolytes, do not have markedly lower surface tension, and do not have significant wetting, foaming, or detergent properties. It is additionally well recognized by those skilled in the art, that sulfonated fatty acids impart improved smear properties, but are very difficult to process into cleansing bars. Also recognized is the fact that alpha sulfonated alkyl esters are too soft and too soluble to produce an acceptable bar alone.

Based on this surprising and unique synergism of alpha sulfonated alkyl esters and sulfonated fatty acids, compositions of the present invention are useful in the production of detergent bars which exhibit improved processability, increased surface tension reduction properties, increased foaming properties, improved color stability, and impart superior feel and after-feel properties to skin.

SUMMARY OF THE INVENTION

The present invention provides compositions suitable for formation into mild personal cleansing or laundry detergent bars. The compositions are useful in preparing stamped, mild personal cleansing and/or laundry detergent bars which have improved processability, are mild to the skin, have improved smear and bar firmness properties, and have good lathering properties. Additionally, compositions of the invention may be utilized to produce dish washing pastes, gels and body washes, along with other uses The compositions of the present invention may take the form of flaked/pellet solids, pastes, liquids, gels, ringing gels, or G-phase concentrates, depending upon the amount of water incorporated therein.

The compositions of the present invention generally comprise:

(a) from about 30% to about 99% by weight of a mixture of an anionic surfactants comprising:
 i) an alpha sulfonated alkyl ester; and
 ii) a sulfonated fatty acid;
(b) from about 0.5% to about 50% by weight of a fatty acid; and
(c) from about 0.1% to about 50% by weight water; wherein the ratio of i) to ii) is from about 10:1 to about 0.5:1; and wherein the ratio of (a) to (b) is about 1:1 to about 11:1.

The compositions of the present invention are generally resistant to hydrolysis of the alpha sulfonated alkyl ester and/or the sulfonated fatty acid.

The compositions of the invention may be processed into ordinary soap bars, "syndet" bars, or "combo" bars with the proper choice of optional components.

The compositions of the invention may be translucent and/or can be processed into translucent personal cleansing and/or laundry detergent bars with the appropriate choice of additional components. The compositions are suitable for processing using extrusion or plodder equipment.

The present invention further provides methods for manufacturing personal cleansing soap bars which employ the inventive compositions. The present invention additionally encompasses the personal cleansing soap bars which comprise the inventive compositions, and processes to manufacture such bars.

DETAILED DESCRIPTION OF THE INVENTION

The present invention relates to compositions suitable for formation into mild personal cleansing or laundry detergent bars comprising:

(a) from about 30% to about 99% by weight of a mixture of an anionic surfactants comprising i) an alpha sulfonated alkyl ester of the formula

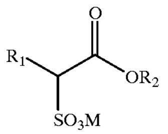

wherein $R_1$ is a $C_6$–$C_{22}$ hydrocarbyl, preferably an alkyl, or combination thereof, $R_2$ is a straight or branched chain $C_1$–$C_6$ hydrocarbyl, preferably an alkyl, or combination thereof, and M is hydrogen or sodium, potassium, calcium, magnesium, monoethanolamine, diethanolamine, triethanolamine, or a mixture thereof; and ii) a sulfonated fatty acid of the formula

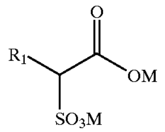

wherein $R_1$ is a $C_1$–$C_{22}$ hydrocarbyl, preferably an alkyl, or combination thereof, and M is hydrogen and/or sodium, potassium, calcium, magnesium, monoethanolamine, diethanolamine, triethanolamine, or a mixture thereof;

(b) from about 0.5% to about 50% by weight of a fatty acid of the formula

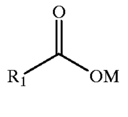

wherein $R_1$ is a $C_6$–$C_{22}$ hydrocarbyl, preferably an alkyl, or combination thereof, and M is hydrogen and/or sodium, potassium, calcium, magnesium, monoethanolamine, diethanolamine, triethanolamine, or a mixture thereof; and (c) from about 0.1% to about 50% by weight water;

wherein the ratio of i) to ii) is from about 10:1 to about 0.5:1; and wherein the ratio of (a) to (b) is about 11:1 to about 1:11.

In a more preferred embodiment of the present invention, the detergent composition comprises:

(a) from about 50% to about 90% by weight of a mixture of an anionic surfactants comprising i) an alpha sulfonated alkyl ester of the formula

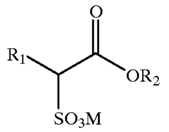

wherein $R_1$ is a $C_{10}$–$C_{18}$ hydrocarbyl, preferably an alkyl, or combination thereof, $R_2$ is a straight or branched chain $C_1$–$C_4$, and M is hydrogen or sodium, potassium, calcium, magnesium, monoethanolamine, diethanolamine, triethanolamine, or a mixture thereof; and ii) a sulfonated fatty acid of the formula

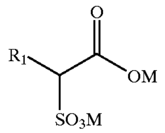

wherein $R_1$ is a $C_{10}$–$C_{18}$ hydrocarbyl, preferably an alkyl, or combination thereof, and M is hydrogen and/or sodium, potassium, calcium, magnesium, monoethanolamine, diethanolamine, triethanolamine, or a mixture thereof;

(b) from about 10% to about 50% by weight of a fatty acid of the formula

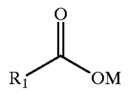

wherein $R_1$ is a $C_{16}$–$C_{18}$ alkyl group, and M is hydrogen and/or sodium, potassium, calcium, magnesium, monoethanolamine, diethanolamine, triethanolamine, or a mixture thereof; and (c) from about 0.1% to about 20% by weight water;

wherein the ratio of i) to ii) is from about 8:1 to about 1:2; and wherein the ratio of (a) to (b) is about 9:1 to about 1:1.

In a most preferred embodiment of the present invention, the detergent composition comprises:

(a) from about 60% to about 80% by weight of a mixture of an anionic surfactants comprising i) an alpha sulfonated alkyl ester of the formula

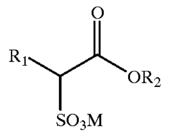

wherein $R_1$ is at least 80% $C_{12}$–$C_{15}$ alkyl, and about 0–20% of a mixture of $C_8$–$C_{10}$ and $C_{16}$–$C_{18}$ alkyl; wherein $R_2$ is methyl, and M is hydrogen or sodium, potassium, calcium, magnesium, monoethanolamine, diethanolamine, triethanolamine, or a mixture thereof; and ii) a sulfonated fatty acid of the formula

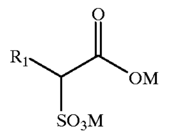

wherein $R_1$ is about 80% $C_{12}$–$C_{15}$ alkyl, and about 20% of a mixture of $C_8$–$C_{10}$ and $C_{16}$–$C_{18}$ alkyl; and wherein M is hydrogen and/or sodium, potassium, calcium, magnesium, monoethanolamine, diethanolamine, triethanolamine, or a mixture thereof;

(b) from about 20% to about 30% by weight of a fatty acid of the formula

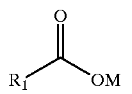

wherein $R_1$ is predominantly a $C_{16}$–$C_{18}$ hydrocarbyl, preferably an alkyl, or combination thereof, and M is hydrogen and/or sodium, potassium, calcium, magnesium, monoethanolamine, diethanolamine, triethanolamine, or a mixture thereof; and (c) from about 0.1% to about 15% by weight water;

wherein the ratio of i) to ii) is from about 7:1 to about 1:1 and wherein the ratio of (a) to (b) is about 4:1 to about 3:2.

The present invention further preferably provides compositions wherein acyl isethionate instead of fatty acid is present as a component. Accordingly, the invention also desirably provides a composition suitable for formation into mild personal cleansing or laundry detergent bars comprising:

(a) from about 50% to about 90% by weight of a mixture of an anionic surfactants comprising i) an alpha sulfonated alkyl ester of the formula

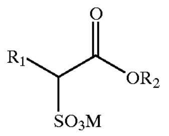

wherein $R_1$ is a $C_6$–$C_{22}$ hydrocarbyl, preferably an alkyl, or combination thereof, $R_2$ is a straight or branched chain $C_1$–$C_6$ hydrocarbyl, preferably an alkyl, or combination thereof, and M is hydrogen or sodium, potassium, calcium, magnesium, monoethanolamine, diethanolamine, triethanolamine, or a mixture thereof; and ii) a sulfonated fatty acid of the formula

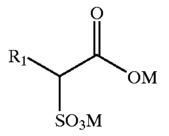

wherein $R_1$ is a $C_{16}$–$C_{22}$ hydrocarbyl, preferably an alkyl, or combination thereof, and M is hydrogen and/or sodium, potassium, calcium, magnesium, monoethanolamine, diethanolamine, triethanolamine, or a mixture thereof;

(b) from about 10% to about 50% by weight of an acyl isethionate of the formula $RCOOCH_2CH_2SO_3^-M^+$ wherein R is a $C_6$–$C_{22}$ hydrocarbyl, preferably an alkyl, or combination thereof, and M is hydrogen, sodium, potassium, calcium, magnesium, monoethanolamine, diethanolamine, triethanolamine, or a mixture thereof; and (c) from about 0.1% to about 20% by weight water; wherein the ratio of i) to ii) is from about 10:1 to about 1:2; and wherein the ratio of (a) to (b) is about 11:1 to about 1:11.

Furthermore, the invention preferably provides a composition suitable for formation into mild personal cleansing or laundry detergent bars comprising:

(a) from about 60% to about 80% by weight of a mixture of an anionic surfactants comprising i) an alpha sulfonated alkyl ester of the formula:

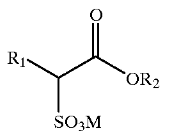

wherein $R_1$ is at least 80% $C_{12}$–$C_{15}$ alkyl, and about 0–20% of a mixture of $C_8$–$C_{10}$ and $C_{16}$–$C_{18}$ alklyl; wherein $R_2$ is methyl, and M is hydrogen or sodium, potassium, calcium, magnesium, monoethanolamine, diethanolamine, triethanolamine, or a mixture thereof; and ii) a sulfonated fatty acid of the formula

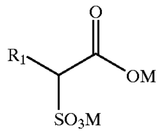

wherein $R_1$ is about 80% $C_{12}$–$C_{15}$ alkyl, and about 20% of a mixture of $C_8$–$C_{10}$ and $C_{16}$–$C_{18}$ alkyl; and wherein M is hydrogen and/or sodium, potassium, calcium, magnesium, monoethanolamine, diethanolamine, triethanolamine, or a mixture thereof;

(b) from about 20% to about 30% by weight of an acyl isethionate of the formula $RCOOCH_2CH_2SO_3^-M^+$ wherein R is a $C_6$–$C_{22}$ hydrocarbyl, preferably an alkyl, or combination thereof, and M is hydrogen, sodium, potassium, calcium, magnesium, monoethanolamine, diethanolamine, triethanolamine, or a mixture thereof; and (c) from about 0.1% to about 15% by weight water;

wherein the ratio of i) to ii) is from about 7:1 to about 1:2; and wherein the ratio of (a) to (b) is about 4:1 to about 3:2.

Compositions of the present invention may additionally contain about 0.1 % to about 10 % by weight of an alkali metal inorganic salt. Generally, without being bound by any particular theory, the alkali metal salt may be any such salt capable of acting as crisping agent or builder to the final bar formulation. More preferably, the alkali metal salt is selected from the group consisting essentially of sodium sulfate, sodium chloride, sodium carbonate, potassium sulfate, potassium chloride, potassium carbonate, calcium sulfate, calcium chloride, calcium carbonate, magnesium sulfate, magnesium chloride, or magnesium carbonate, or mixtures thereof. In a more preferred embodiment of the present invention the alkali metal salt is magnesium chloride and is present from about 1.0% to about 8.0% by weight in the composition.

Additionally, the present compositions may further comprise from about 1% to about 5% by weight paraffin. The compositions also optionally may further comprise additional ingredients including from about 0.5% to about 10% by weight of a sucrogylceride, a functional metallic soap, a succinamate, a sulfosuccinamate, a mono-, di-, or trigylceride, chitosan, or a mixture thereof. Similarly, the compositions may further comprise from about 0.1% to about 10% by weight of fragrance, emollients, moisturizers, viscosity control agents, as well as additional agents appropriate for incorporation into a composition of the invention and which are known to those skilled in the art.

The compositions of the present invention may be transparent and/or produce a transparent mild personal cleansing or laundry detergent bar upon proper processing and/or selection of optional ingredients and components detailed herein. Additionally, the compositions may be used to produce a transparent dish washing gel, paste or solution, or further applications such as are apparent to one skilled in the art. Whether transparent or nontransparent, the compositions may exist as solid flakes, or as a gel.

The compositions typically contain an amount of water sufficient to providing a melting point of the composition of between about 60° C. and about 80° C. Such a melting point provides for easy pumping and readily allows for methanol and water evaporation without the excessive foaming that is characteristic of conventional alpha sulfonated alkyl ester/fatty acid blends.

All numerical limits, ranges, ratios, etc., are approximations ("abouts") unless otherwise specified. Within the scope of the invention, there are several different preferred embodiments.

The term "soap" as used herein includes the plural as well as the singular in terms of mixed ions and fatty acid chains unless otherwise specified.

The terms "coconut oil" (CNO); "palm kernel oil" (PKO); "palm oil stearin" (POS); and "tallow" (T) as used herein refer to a mixture of soaps having an approximate chain length distribution as usually defined in the literature; unless otherwise specified.

Alpha Sulfonated Alkyl Esters and Alpha Sulfonated Fatty Acids

The compositions of the present invention typically contain from about 30% to about 99% by weight of a mixture of an anionic surfactants comprising an alpha sulfonated alkyl ester and a sulfonated fatty acid. The alpha sulfonated alkyl esters used in the invention are typically prepared by sulfonating an alkyl ester of a fatty acid with a sulfonating agent such as $SO_3$, followed by neutralization with a base, such as sodium hydroxide, potassium hydroxide, calcium hydroxide, magnesium oxide, monoethanolamine, diethanolamine or triethanolamine, or a mixture thereof. When prepared in this manner, the alpha sulfonated alkyl esters normally contain a minor amount, typically not exceeding 33% by weight, of alpha sulfonated fatty acid, i.e., disalt, which results from hydrolysis of the ester. Generally, larger amounts of the disalt are obtained by hydrolyzing a known amount of the monosalt; hydrolysis may be accomplished in situ during the preparation of the composition. Accordingly, the alpha sulfonated alkyl ester and alpha sulfonated fatty acid may be provided to the composition as a blend of components which naturally result from the sulfonation of an alkyl ester of a fatty acid, or as individual components. Furthermore, it is known to one skilled in the art that minor impurities such as sodium sulfate, unsulfonated methyl esters (ME), and unsulfonated fatty acids (FA) may also be present in the mixtures according to the invention.

The alpha sulfonated alkyl esters, i.e., alkyl ester sulfonate surfactants, include linear esters of $C_6$–$C_{22}$ carboxylic acid (i.e., fatty acids) which are sulfonated with gaseous $SO_3$ according to the "The Journal of American Oil Chemists Society," 52 (1975), pp. 323–329. Suitable starting materials include, among others, natural fatty substances as derived from tallow, palm oil, etc.

In particular, preferably the α-sulfonated alkyl ester is a sulfonated methyl ester, desirably as further described herein. Accordingly, the present invention preferably provides a composition wherein the alpha sulfonated alkyl ester is of the formula

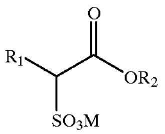

wherein $R_1$ is about 80% $C_{12}$–$C_{15}$ alkyl, and about 20% of a mixture of $C_8$–$C_{10}$ and $C_{16}$–$C_{18}$ alkyl; wherein $R_2$ is methyl, and M is hydrogen or sodium, potassium, calcium, magnesium monoethanolamine, diethanolamine, triethanolamine, or a mixture thereof.

The invention further preferably provides a composition wherein the sulfonated fatty acid is of the formula

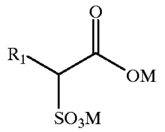

wherein $R_1$ is at least 80% $C_{14}$–$C_{16}$ alkyl, and about 0–20% of a mixture of $C_{10}$–$C_{13}$ and $C_{17}$–$C_{18}$ alkyl; and wherein M is hydrogen and/or sodium, potassium, calcium, magnesium monoethanolamine, diethanolamine, triethanolamine, or a mixture thereof.

Fatty Acids

The compositions of the invention typically contain from about 0.5% to about 50% by weight of a fatty acid. The (free) fatty acids preferably used in the present invention correspond with the fatty acids used to make conventional soaps. The fatty acid material which is desirably incorporated into the present invention includes material ranging in hydrocarbon chain length of from about 6 to about 22, essentially saturated. These fatty acids can be highly purified individual chain lengths and/or crude mixtures such as those derived from fats and oils. The industry term "triple pressed stearic acid" comprises about 45 parts stearic and 55 parts palmitic acids. Additionally, the term stearic acid is used in the context of the soap industry to refer to a fatty acid mixture which is predominately stearic acid. Thus, this is its meaning as used herein.

The composition may include soaps derived from hydrocarbon chain lengths of from about 6 to about 22 (including carboxyl carbon) and are preferably saturated. It is preferred that the soap be the sodium salt, but other soluble soap can be used. Potassium, calcium, magnesium, monoethanolammonium, diethanolammonium, triethanolammonium, and mixtures thereof, are deemed acceptable. The scaps are preferably prepared by the in situ saponification or ion exchange with halide salt of the corresponding fatty acids, but they may also be introduced as preformed soaps.

Composition pH

Although not critical, the soap compositions herein will preferably be formulated such that they will have a pH of betveen about 4.0 and about 10.0, more preferably between about 5 and about 9.5. Techniques for controlling pH at recommended usage levels include the use of buffers, alkali, acids, etc., and are well known to those skilled in the art.

Optional Components

Synthetic Detergent Surfactants

The present invention encompasses the optional use of additional synthetic detergent surfactants, such as for example, acyl isethionates, e.g, sodium acyl (cocoyl) isethionate (SCI). A preferred SCI is "STCI" herein defined as "sodium topped coconut isethionate" which is further defined as SCI with alkyl carbon chains having: 0% to 4% of highly soluble acyl groups ($C_6$, $C_8$, $C_{10}$, $C_{18:1}$, and $C_{18:2}$), 45–65% $C_{12}$, and 30%–55% $C_{14}$, $C_{16}$, $C_{18}$. The terms SCI and STCI are used interchangeably herein unless otherwise specified.

Additional optional detergent surfactants include, among others, anionic, zwitterionic, amphoteric, semi-polar nonionic, or nonionic, or mixtures thereof.

Examples of useful optional anionic surfactants include, among others, the sodium, potassium, magnesium, calcium, ammonium, monoethanolammonium (MEA), diethanolammonium (DEA), triethanolammonium (TEA), or alkyl amine salts, or mixtures thereof, of sulfonic acids, polysulfonic acids, sulfonic acids of oils, paraffin sulfonic acids, lignin sulfonic acids, petroleum sulfonic acids, tall oil acids, olefin sulfonic acids, hydroxyolefin sulfonic acids, polyolefin sulfonic acids, polyhydroxy polyolefin sulfonic acids, perfluorinated carboxylic acids, alkoxylated carboxylic acid sulfonic acids, polycarboxylic acids, polycarboxylic acid polysulfonic acids, alkoxylated polycarboxylic acid polysulfonic acids, phosphoric acids, alkoxylated phosphoric acids, polyphosphoric acids, and alkoxylated polyphosphoric acids, fluorinated phosphoric acids, phosphoric acid esters of oils, phosphinic acids, alkylphosphinic acids, aminophosphinic acids, polyphosphinic acids, vinyl phosphinic acids, phosphonic acids, polyphosphonic acids, phosphonic acid alkyl esters, α-phosphono fatty acids, oragnoamine polymethylphosphonic acids, organoamino dialkylene phosphonic acids, alkanolamine phosphonic acids, trialkyledine phosphonic acids, acylamidomethane phosphonic acids, alkyliminodimethylene diphosphonic acids, polymethylene-bis (nitrilo dimethylene)tetraphosphonic acids, alkyl bis (phosphonoalkylidene) amine oxide acids, esters of substituted aminomethylphosphonic acids, phosphonamidic acids, acylated amino acids (e.g., amino acids reacted with alkyl acyl chlorides, alkyl esters or carboxylic acids to produce N-acylamino acids), N-alkyl acylamino acids, acylated protein hydrolysates, branched alkylbenzene sulfonic acids, alkyl gylceryl ether sulfuric acid esters, alkyl sulfuric acid esters, alkoxylated alkyl sulfuric acid esters, α-sulfonated ester diacids, alkoxylated α-sulfonated alkyl ester acids, α-sulfonated dialkyl diester acids, di-α-sulfonated dialkyl diester acids, α-sulfonated alkyl acetate acids, primary and secondary alkyl sulfonic acids, perfluorinated alkyl sulfonic acids, sulfosuccinic mono- and diester acids, polysulfosuccinic polyester acids, sulfoitaconic diester acids, sulfosuccinamic acids, sulfosuccinic amide acids, sulfosuccinic imide acids, phthalic acids, sulfophthalic acids, sulfoisophthalic acids, phthalamic acids, sulfophthalamic acids, alkyl ketone sulfonic acids, hydroxyalkanc-1-sulfonic acids, lactoie sulfonic acids, sulfonic acid amides, sulfonic acid diamides, alkyl phenol sulfuric acid esters, alkoxylated alkyl phenol sulfuric acid esters, alkylated cycloalkyl sulfuric acid esters, alkoxylated alkylated cycloalkyl sulfuric acid esters, dendritic polysulfonic acids, dendritic polycarboxylic acids, dendritic polyphosphoric acids, sarcosinic acids, isethionic acids, tauric acids, fluorinated carboxylic acids, fluorinated sulfonic acids, fluorinated sulfate acids, fluorinated phosphonic and phosphinic acids, and mixtures thereof.

Suitable optional nonionic surfactants in accordance with the present invention are generally disclosed in U.S. Pat. No. 3,929,678, Laughlin et al., issued Dec. 30, 1975, at column, 13 line 14 through column 16, line 6, incorporated herein by reference. Generally, the nonionic surfactant is selected from the group comprising polyoxyethyleneated alkylphenols, polyoxyethyleneated straight chain alcohols, polyoxyethyleneated branched chain alcohols, polyoxyethyleneated polyoxypropylene glycols, polyoxyethyleneated mercaptans, fatty acid esters, glyceryl fatty acid esters, polyglyceryl fatty acid esters, propylene glycol esters, sorbitol esters, polyoxyethyleneated soibitol esters, polyoxyethylene glycol esters, polyoxyethyleneated fatty acid esters, primary alkanolamides, ethoxylated primary alkanolamides, secondary alkanolamides, ethoxylated secondary alkanolamides, tertiary acetylenic glycols, polyoxyethyleneated silicones, N-alkylpyrrolidones, alkylpolyglycosides, alkylpolylsaccharides, EO-PO block polymers, polyhydroxy fatty acid amides, amine oxides and mixtures thereof. Further, exemplary, non-limiting classes of useful nonionic surfactants are listed below:

1. The polyethylene, polypropylene, and polybutylene oxide condensates of alkyl phenols. In general, the polyethylene oxide condensates are preferred. These compounds include the condensation products of alkyl phenols having an alkyl group containing from about 6 to 12 carbon atoms in either a straight or branched chain configuration with the alkylene oxide. In a preferred embodiment, the ethylene oxide is present in an amount equal to from about 1 to about 25 moles of ethylene oxide per mole of alkyl phenol. Commercially available nonionic surfactants of this type include Igepal® CO-630, marketed by the GAF Corporation; and Triton® X-45, X-114, X-100 and X-102, all marketed by the Rohm and Haas Company.

2. The condensation products of aliphatic alcohols with from about I to about 25 moles of ethylene oxide. The alkyl chain of the aliphatic alcohol can either be straight or branched, primary or secondary, and generally contain from about 8 to about 22 carbon atoms. Particularly preferred are the condensation products of alcohols having an alkyl group containing from about 6 to about 11 carbon atoms with from about 2 to about 10 moles of ethylene oxide per mole of alcohol. Examples of commercially available nonionic surfactants of this type include Tergitol® 15-S-9 (the condensation products of $C_{11}$–$C_{15}$ linear alcohol with 9 moles of ethylene oxide), Tergitol® 24-L-6 NMW (the condensation products of $C_{12}$–$C_{14}$ primary alcohol with 6 moles of ethylene oxide with a narrow molecular weight distribution), both marketed by Union Carbide Corporation; Neodol® 91-8 (the condensation product of $C_9$–$C_{11}$ linear alcohol with 8 moles of ethylene oxide), Neodol® 23-6.5 (the condensation product of $C_{12}$–$C_{13}$ linear alcohol with 6.5 moles of ethylene oxide), Neodol® 45-7 (the condensation product of $C_{14}$–$C_{15}$ linear alcohol with 7 moles of ethylene oxide), Neodol® 91-6 (the condensation product of $C_9$–$C_{11}$ linear alcohol with 6 moles of ethylene oxide), marketed by Shell Chemical Company, and Kyro® EOB (the condensation product of $C_{13}$–$C_{15}$ linear alcohol with 9 moles of ethylene oxide), marketed by the Procter and Gamble Company.

3. The condensation products of ethylene oxide with a hydrophobic base formed by the condensation of propylene oxide with propylene glycol. The hydrophobic portion of these compounds preferably has a molecular weight of from about 1500 to about 1880 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic® surfactants, marketed by BASF.

4. The condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic® compounds, marketed by BASF.

5. Semi-polar nonionic surfactants are a special category of nonionic surfactants which include water-soluble amine oxides containing on alkyl moiety of from about 10 to about 18 carbon atoms and 2 moieties selected from the group comprising alkyl groups and hydroxyalkyl groups containing from about 1 to about 3 carbon atoms; and water-soluble sulfoxides containing alkyl moieties of from about 10 to about 18 carbon atoms and a moiety selected from the group comprising alkyl groups and hydroxyalkyl groups of from about 1 to about 3 carbon atoms.

6. Alkylpolysaccharides disclosed in U.S. Pat. No. 4,565,647, Lenado, issued Jan. 21, 1986, incorporated herein by reference, having a hydrophobic group containing from about 6 to about 30 carbon atoms, preferably from about 10 to about 16 carbon atoms and a polysaccharide, e.g., a polyglucoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally, the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6- positions on the preceding saccharide units.

7. An ethyl ester ethoxylate and/or alkoxylate such as those described in U.S. Pat. No. 5,220,046, incorporated herein by reference. These material may be prepared according to the procedure set forth in Japanese Kokai patent application No. HEI 5 [1993]-22396. For example, they may be prepared by a one-step condensation reaction between an alkyl ester and an alkylene oxide in the present of a catalytic amount of magnesium together with another ion selected from the group of $Al^{+3}$, $Ga^{+3}$, $In^{+3}$, $Co^{+3}$, $Sc^{+3}$, $La^{+3}$ and $Mn^{+3}$. Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched, containing from about 8 to about 18, preferably from about 12 to about 14 carbon atoms; n is 2 or 3, preferably 2; t is from about 0 to about 10, preferably 0; and x is from about 1.3 to about 10, preferably from about 1.3 to 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glucosyl units can then be attached between their 1-position and the preceding glycosyl units 2-, 3-, 4-, and/or 6-position, preferably predominately the 2-position.

Suitable optional amphoteric surfactants are selected from the group comprising alkyl glycinates, propionates, imidazolines, amphoalkylsulfonates sold as "Miranol"® by Rhone Poulenc, N-alkylaminopropionic acids, N-alkyliminodipropionic acids, imidazoline carboxylates, N-alkylbetaines, amido propyl betaines, sarcosinates, cocoamphocarboxyglycinates, amine oxides, sulfobetaines, sultaines and mixtures thereof Additional suitable amphoteric surfactants include cocoamphoglycinate, cocoamphocarboxyglycinate, lauramphocarboxyglycinate, cocoamphopropionate, lauramphopropionate, stearamphoglycinate, cocoamphocarboxypropionate, tallowamphopropionate, tallowamphoglycinate, oleoamphoglycinate, caproamphoglycinate, caprylamphopropionate, caprylamphocarboxyglycinate, cocoyl imidazoline, lauryl imidazoline, stearyl imidazoline, behenyl imidazoline, behenylhydroxyethyl imidazoline, capryamphopropylsulfonate, cocamphopropylsulfonate, stearamphopropylsulfonate, oleoamphopropylsulfonate and the like.

Optional amine oxide surfactants which are generally suitable for use in the present invention are alkylamine and amidoamine oxides. Examples of betaines and sultaines which are suitable for use in the present invention are alkyl betaines and sultaines sold as “Mirataine”® by Rhone Poulenc , “Lonzaine”® by Lonza, Inc., Fairlawn, N. J. Examples of betaines and sultaines are cocobetaine, cocoamidoethyl betaine, cocoamidopropyl betaine, lauryl betaine, lauramidopropyl betaine, paimamidopropyl betaine, stearamidopropyl betaine, stearyl betaine, coco-sultaine, lauryl sultaine, tallowamidopropyl hydroxysultaine and the like.

Optional pH adjusting agents are selected from the group comprising citric acid, succinic acid, phosphoric acid, sodium hydroxide, sodium carbonate, etc.

Optional sequestering agents are selected from the group comprising disodium ethylenediamine tetraacetate.

Additional optional auxiliary surfactants are selected from the group comprising amides, amine oxides, betaines, sultaines and $C_8$–$C_{18}$ fatty alcohols.

Examples of optional amine oxides in the present invention include long-chain amine oxides, i.e., those compounds having the general formula

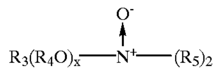

wherein $R_3$ is selected from an alkyl, hydroxyalkyl, acylamidopropyl and alkyl phenyl group, or mixtures thereof, containing from about 8–26 carbon atoms, preferably from about 8–16 carbon atoms; $R_4$ is an alkylene or hydroxyalkylene group containing from about 2–3 carbon atoms, preferably 2 carbon atoms, or mixtures thereof, x is from about 0–3, preferably 0; and each $R_5$ is an alkyl or hydroxyalkyl group containing from about 1–3, preferably from about 1–2 carbon atoms, or a polyethylene oxide group containing from about 1–3, preferably 1, ethylene oxide groups. The $R_5$ groups can be attached to each other, e.g., through an oxygen or nitrogen atom, to form a ring structure.

Preferred optional amine oxide surfactants in particular include $C_{10}$–$C_{18}$ alkyl dimethlyl amine oxides and $C_8$–$C_{12}$ alkoxy ethyl dihydroxyethyl amine oxides. Examples of such materials include dimethyloctylamine oxide, diethyldodecylamine oxide, bis-(2-hydroxyethyl)dodecylamine oxide, dimethyldodecylamine oxide, dodecylamidopropyl dimethylamine oxide and dimethyl-2-hydroxyoctadecylamine oxide. Preferred are $C_{10}$–$C_{18}$ alkyl dimethylamine oxide, and $C_{10}$–$C_{18}$ acylamido alkyl dimethylamine oxide.

Optional betaines useful surfactants in the present invention include compounds having the formula $R(R_1)_2N^+ R_2COO^-$ wherein R is a $C_6$–$C_{18}$ hydrocarbyl group, preferably $C_{10}$–$C_{16}$ alkyl group, each $R_1$ is typically $C_1$–$C_3$, alkyl, preferably methyl, and $R_2$ is a $C_1$–$C_5$ hydrocarbyl group, preferably a $C_1$–$C_5$ alkylene group, more preferably a $C_1$–$C_2$ alkylene group. Examples of suitable betaines include coconut acylamidopropyldimethyl betaine; hexadecyl dimethyl betaine; $C_{12}$–$C_{14}$ acylamidopropylbetaine; $C_8$–$C_{14}$ acylamidohexyldiethyl betaine; 4-[$C_{14}$–$C_{16}$ acylmethylamidodiethylammonio]-1-carboxybutane; $C_{16}$–$C_{18}$ acylamidododimethylbataine; $C_{12}$–$C_{16}$ acylamidopentanediethylbetaine; $C_{12}$–$C_{16}$ acylmethylamidodimethylbetaine. Preferred betaines are $C_{12}$–$C_{18}$ dimethylamoniohexanoate and the $C_{10}$–$C_{18}$ acylamidopropane (or ethane) dimethyl (or diethyl) betaines.

Optional sultaines useful surfactants in the present invention include compounds having the formula $R(R_1)_2N^+ R_2SO_3^-$, wherein R is a $C_6$–$C_{18}$ hydrocarbyl group, preferably a $C_{10}$–$C_{16}$ alkyl group, more preferably a $C_{12}$–$C_{13}$ alkyl group; each $R_1$ is typically $C_1$–$C_3$ alkyl, preferably methyl and $R_2$ is a $C_1$–$C_6$ hydrocabyl group, preferably a $C_1$–$C_3$ alkylene or, preferably, hydroxyalkylene group. Examples of suitable sultaines are $C_{12}$–$C_{14}$ dihydroxyethylammino propane sulfonate, and $C_{16}$–$C_{18}$ dimethylammonio hexane sulfonate, with $C_{12}$–$C_{14}$ amido propyl ammonio-2-hydroxypropyl sultaine being preferred.

Fatty acid amide surfactants are also optional components of the present invention. Preferred amides are $C_8$–$C_{20}$ alkanol amides, monoethanolamides, diethaniolamides and isopropanolamides. A particularly preferred amide is a mixture of myristic monoethaolamide and lauric monoethanolamide. This preferred amide is sold by Stepan Company, Northfield, Ill. as Ninol LMP.

Other optional ingredients for use in the present compositions include non-volatile, nonionie silicone conditioning agents, polyalkyl or polyaryl siloxanes, and pearlescent/suspending agents, detergent builders, cellulase enzymes, softening clays, smectite-type softening clays, polymeric clays, flocculating agents, dye transfer inhibitors, and optical brighteners.

Polyols

Optional polyols, such as glycerin, may be incorporated in the compositions of the present invention. The compositions of the present invention can optionally contain from about 0.5% to about 5.0% by weight of glycerine or polyol; preferably from about 1.0% to about 3.0%, more preferably, from about 1.0% to about 1.8%. The useful polyols of the present invention are generally liquid water-soluble aliphatic polyols or polyethylene glycols or polypropylene glycols. The polyol may be saturated or contain ethylenic linkages; it must have at least two alcohol groups attached to separate carbon atoms in the chain, and must be water soluble and liquid at room temperature. If desired, the compound may have an alcohol group attached to each carbon atom in the chain. Among the compounds which are effective are ethylene glycol, propylene glycol, glycerin and mixtures thereof. A preferred polyol is glycerin. Water-soluble polyethylene glycols, water-soluble polypropylene glycols useful in the present invention are those products produced by the condensation of ethylene glycol molecules or propylene glycol molecules to form high molecular weight ethers having terminal hydroxyl groups. The polyethylene glycol compounds may range from diethylene glycol to those having molecular weights as high as about 800, preferably, about 100 to 700, more preferably, 100 to 600. Normally, polyethylene glycols having molecular weights up to 800 are liquid and completely soluble in water. As the molecular weight of the polyethylene glycol increases beyond 800, they become solid and less water-soluble. Such solids may be used as plasticizers herein when malleable at 35° C. to about 46° C. The polypropylene glycol compounds useful in this invention may range from dipropylene glycol to polypropylene glycols having molecular weights of about 2000, preferably less than 1500, more preferably, less than 1000. These are normally liquid at room temperature and are readily soluble in water.

Paraffins and Waxes The compositions of the present invention may optionally contain about 1.0% to about 15.0% by weight of wax, preferably paraffin, having a melting point of from about 54° C. to about 180° C. The waxes are selected from the group consisting of beeswax, spermaceti, camauba, bayberry, candelilla, montan, ozokerite, ceresin, paraffin, synthetic waxes such as Fisher-Tropsch waxes, microcrystalline wax, and mixtures thereof. The wax ingredient is used in the product to impart skin mildness, plasticity, firmness, and processability. It also provides a glossy look and smooth feel to the bar.

A highly preferred component of this invention is a wax, preferably paraffin wax having a melting point of from about 54° C. to about 82° C., preferably from about 60° C. to about 74° C., and most preferably from about 61° C. to about 71° C. "High melt" paraffin is paraffin that has a melting point from about 66° C. to about 71° C. "Low melt" paraffin is paraffin that has a melting point from about 54° C. to about 60° C. A preferred paraffin wax is a fully refined petroleum wax which is odorless and tasteless and meets FDA requirements for use as coatings for food and food packages. Such paraffins are readily available commercially. A very suitable paraffin can be obtained, for example, from The National Wax Co. under the trade name 6975.

Cationic Polymers

The compositions of the present invention can optionally contain from about 0.5% to about 2.0% by weight of a suitably fast hydrating cationic polymer. The polymers have molecular weights of from about 1,000 to about 5,000,000. The cationic polymer (skin conditioning agent) is selected, e.g., from the group consisting of: (I) cationic polysaccharides; (II) cationic copolymers of saccharides and synthetic cationic monomers, and (III) synthetic polymers selected from the group consisting of: (A) cationic polyalkylene imines; (B) cationic ethoxy polyalkylene imines; and (C) cationic poly[N-[-3-(dimethylammonio)propyl]-N'-[3-(ethyleneoxyethylene dimethylammonio)propyl]urea dichloride].

Plasticizers

The compositions of the present invention can optionally contain from about 1.0% to about 5.0% by weight of plasticizers. The plasticizers may be comprised of solid aliphatic materials. E.g. fatty alcohols, paraffins, monoglycerides, diglycerides, triglycerides, alkali soaps, alkaline soaps, or high molecular weight (solid) hydrophilic materials, e.g. polyethylene glycols, polypropylene glycols, starches, sugars and/or mixtures thereof.

Other Optional Ingredienits

Other ingredients of the present invention are selected for the various applications. E.g., perfumes can be used in formulating the skin cleansing products, generally at a level of from about 0.1 parts to about 1.5 parts of the composition. Vegetable oils, such as peanut and soybean oil, can be added at levels up to 10 parts, preferably 2–6 parts. Alcohols, hydrotropes, colorants, and fillers such as talc, clay, calcium carbonate, oils and dextrin can also be used at appropriate levels. Preservatives, e.g., trisodium etidronate and sodium ethylenediaminetetraacetate (EDTA), generally at a level of less than 1 parts of the composition, can be incorporated in the cleansing products to prevent color and odor degradation. Antibacterials can also be incorporated, usually at levels up to 1.5 parts. Salts, both organic and inorganic, can be incorporated. Examples include sodium chloride, sodium isethionate, sodium sulfate, and their equivalents.

Optional Adjunct Odor-Reducing or Odor-Controlling Materials

The compositions and articles of this invention can also contain an effective, i.e., odor-controlling, amount of various additional aluminosilicate and non-aluminosilicatc odor-controlling materials to further expand their capacity for controlling odors, as well as the range of odor types being controlled. Such materials include, for example, cetyl pyridinium chloride, zinc chloride, EDTA, etidronate, BHT, and the like.

A preferred aluminosilicate is substantially free of particles sized greater than 30 microns, and in fact is substantially free of particles sized over 15 microns for acceptable bar feel. "Substantially free" means that the larger particles arc less than about 5 parts, preferably less than about 4 parts, more preferably less than about 3 parts, as measured by laser light scattering.

Optional Skin-Feel Enhancement Materials

The compositions and articles of this invention may contain an effective, i.e., skin softening and/or moisturizing, amount of various skin feel agents. These skin feel agents include, for example, chitan, triglycerides, glycerine, succinamates, sucroglycerides, and functional metallo-soaps. Suitable sucroglycerides are generally described in Pat. App. No. 96933018.2 (PCT/US96/14740) incorporated herein by reference. Suitable functional metallo-soaps are generally described in U.S. Pat. No. 4,921,942 (to Stepan Company), incorporated herein by reference.

While compositions of the present invention are extremely useful in soap bar and laundry bar applications, other applications for these compositions are possible. The compositions of the present invention may be useable in or as liquid, paste or gel dish washing compositions, hand soaps including waterless hand cleaners, multi-purpose cleaners, body washes, further laundry detergent compositions such as laundry powder, pre-spotter or stain sticks, textile treatment compositions including triethanolamine (TEA) soaps for dry cleaning, shampoos including those for humans, pets, and carpets, car wash, soap scouring pads and scrubbing pads, toilet tank drop ins and/or cleaners, personal care creams and lotions, and the like.

The definitions, abbreviations, and CTFA designations used in the present invention are as set forth in Table 1.

TABLE 1

| Definitions, Abbreviations, and CTFA Designations | |
|---|---|
| BHT | 2,6-di-butyl-4-methyl phenol |
| BHA | 3-tert-4-hydroxyanisole |
| Coco Fatty Acid | Emery 627 (a tradename from Emery Corporation, a division of Henkel) and coconut fatty acids that can be substituted for Emery 627 |
| EDTA | ethylenediamine tetraacetic acid |
| Hyamine | di-isobutyl-phenoxy-ethoxy-ethyl-dimethyl-benzyl ammonium chloride |
| MC-48 | average 6:1 mixture (i.e., ranging from 5:1 to 7:1) of sulfonated stripped coco methyl esters and coco fatty acids |
| Pristerene 4981 | Stearic Acid (from Unichema); approximate iodine value of 1.0 max.; mixture of about 65% $C_{18}$ fatty acid, about 28% $C_{16}$ fatty acid and about 2% myristic fatty acid |
| SFA | disalt; α-sulfonated fatty acid (e.g., that results from hydrolysis of SME) |
| SME | monsalt; α-sulfonated alkyl ester (e.g., α-sulfonated methyl ester) |
| UA | unreacted methyl ester |

All documents, e.g., patents and journal articles, cited above or below are hereby incorporated by reference in their entirety. In the following examples, all amounts are stated in percent by weight of active material unless indicated otherwise. One skilled in the art will recognize that modifications may be made in the present invention without deviating from the spirit or scope of the invention. The invention is illustrated further by the following examples which are not to be construed as limiting the invention or scope of the specific procedures or compositions described herein. All levels and ranges, temperatures, results etc., used herein are approximations unless otherwise specified.

EXAMPLE # 1

Monosalt (SME) MC-48 Preparation

MC-48 as defined above is commercially available from a variety of sources. Its method of manufacture is well known to those skilled in the art.

EXAMPLE #2

Disalt (SFA) Preparation

Approximately 3500 grams of MC-48 acid was placed in a 4 L beaker and with rapid aggitation, approximately 330 grams of sodium hydroxide was added slowly. Upon complete addition of the sodium hydroxide, the resulting SFA material had a thick, pasty consistency. The crude SFA was re-crystallized by washing with methanol, water and salting out the purified SFA product. The crude SFA was analyzed by titrating the material with 0.02N hyamine, which indicated that approximately 46.6% disodium salt of MC-48 was present. The recrystallized SFA product was approximately 99.8% disodium salt of MC-48.

EXAMPLE #3

1:1 Ratio of SME to SFA Sample Preparation

Approximately 138.5 grams of MC-48 acid was added to a 1 L resin kettle, equipped with heating means, aggitation means, pH measurement means and a nitrogen sweep. The acid was heated to 55° C. and approximately 18.7 g of sodium hydroxide powder was added in small portions. As the sodium hydroxide was added an exotherm of 55° C. to about 71° C. occurred, during which time cooling was provided to keep the mixture below approximately 80° C. Near the end of the sodium hydroxide addition, the mixture became very thick and approximately 15.6 grams of methanol was added to keep the mixture semi-fluid. The final product was a paste at room temperature, i.e. 25° C. The final SFA/SME product was titrated with 0.02N hyamine which showed the material to be approximately 41.65% SME (mono salt) and approximately 40.34% SFA (disalt).

EXAMPLE #4

2:1 Ratio SME to SFA Sample Preparation

Approximately 53.4 grams of undigested α-sulfomethyl ester acid was placed in a 500 mL 4-neck flask, equipped with a heating means, a consensor and stirring means. The acid was heated to 130° C. for 1 minute to digest the acid. The acid was cooled after digestion to 75° C., and approximately 5.3 grams of anhydrous methanol was added, which produced an exotherm to approximately 85° C. Next, approximately 6.4 grams hydrogen peroxide (35% soln.) was added and the resulting mixture heated to about 120° C. for about 5 minutes. After this period of time, the mixture was cooled to about 60° C. and 8.82 grams water was added, producing a gel-like mixture. The mixture was then further cooled to 40° C. and sodium hydroxide (50% soln.) was added dropwise until a pH of 6 was achieved. The final product was a soft, flowable, yellow gel. The actives were determined, via titration with 0.02N hyamine, to be 46.3% SME (monosalt) and 22.5 SFA (disalt).

EXAMPLE #5

25:1 Ratio SME to SFA Sample Preparation

Approximately 50 grams of undigested α-sulfomethyl ester acid was placed in a 500 mL round bottom flask and heated to 130° C. for 1 minute using a hot oil bath. A mechanical stirrer with a glass shaft and teflon blade was used to ensure thorough mixing. The apparatus included a condenser (allihn type) to prevent loss of any solvent vapors. The acid was cooled after digestion to 70° C., and approximately 5.3 grams of anhydrous methanol was added and thoroughly combined. This was followed by the addition of approximately 1.825 grams hydrogen peroxide (50% soln.) and heating of the resulting mixture to about 89° C. for about 64 minutes. After this period of time, the mixture was cooled to about 40° C. and 64.7 grams water was added and mixed thoroughly. The acid was neutralized by the dropwise addition of sodium hydroxide (50% soln) until a pH of about 6.5 was achieved, all the while maintaining the temperature below 45° C. using a water/ice bath. The final product was analyzed by titration with 0.02N hyamine, and found to comprise 35.82% SME (monosalt) and 1.36 SFA (disalt), with the SME:SFA ratio being 26.3:1.

EXAMPLE #6

Preparation of Samples Containing Various Amounts of SME and SFA

In general, samples containing differing amounts of SFA and SME (e.g., total amounts of each or either present in the mixture, and optionally present with respect to varying amounts of total SFA and SME actives) can be obtained, for instance, by varying the hydrolysis of SME to SFA (e.g., by varying hydrolysis conditions, and/or amount of methanol applied for hydrolysis). Similarly, mixtures can be combined, and/or varying amounts of either pure (or relatively pure) SME or SFA can be added to adjust the concentration of a particular mixture. One skilled in the art would easily know how to obtain the particular ratios referenced herein (if not otherwise disclosed) as well as further ratios and formulations encompassed by the scope of the invention.

EXAMPLE #7

Characterization of Foaming Properties

Foaming measurements of samples prepared according to the invention were obtained. The samples were prepared as set forth in Table 2, and as further described in subsequent examples. In particular, the samples tested for foaming contained amounts of SFA (% of total actives) ranging from about 4%, to 96%, wherein the SME/SFA ratios correspondingly vary from about 23/1 to about 1/22 (i.e., as set forth in Table 2).

TABLE 2

Formulations of Samples Containing Various Amounts of SFA

| Ingredients | Actives % | 2020–92–1 % | 2020–92–2 % | 2020–92–3 % | 2020–92–4 % | 2020–92–5 % | 2020–92–6 % | 2020–92–7 % | 2020–92–8 % |
|---|---|---|---|---|---|---|---|---|---|
| Soap Base | 100 | 75.17 | 75.17 | 75.17 | 75.17 | 75.17 | 75.17 | 75.17 | 75.17 |
| SME | 100 | 13.57 | 12 | 10.01 | 8.01 | 6.01 | 4.01 | 2 | 0.6 |

TABLE 2-continued

Formulations of Samples Containing Various Amounts of SFA

| Ingredients | Actives % | 2020–92–1 % | 2020–92–2 % | 2020–92–3 % | 2020–92–4 % | 2020–92–5 % | 2020–92–6 % | 2020–92–7 % | 2020–92–8 % |
|---|---|---|---|---|---|---|---|---|---|
| SFA | 100 | 0.6 | 1.6 | 3.3 | 5.4 | 7.6 | 9.7 | 11.9 | 13.4 |
| $MgCl_2$ | 100 | 0.66 | 0.66 | 0.66 | 0.66 | 0.66 | 0.66 | 0.66 | 0.66 |
| Stearic Acid | 100 | 2 | 2 | 2 | 2 | 2 | 2 | 2 | 2 |
| Water | 100 | 8 | 8.57 | 8.86 | 8.76 | 8.56 | 8.46 | 8.27 | 8.17 |
| TOTAL | 100 | 100 | 100 | 100 | 100 | 100 | 100 | 100 | 100 |
| Synthetic Surfactant Relationship | | | | | | | | | |
| SFA (%) | 100 | 4 | 12 | 25 | 40 | 56 | 71 | 86 | 96 |
| SME (%) | 100 | 96 | 88 | 75 | 60 | 44 | 29 | 14 | 4 |
| TOTAL | | 100 | 100 | 100 | 100 | 100 | 100 | 100 | 100 |
| SME/SFA ratio | | 22.61/1 | 7.5/1 | 3.03/1 | 1.48/1 | 1/1.26 | 1/2.42 | 1/5.95 | 1/22.3 |

The soap base described in Table 2 is Prisavon 9220 supplied by Unichema, and is made of a sodium salt of tallow/coconut 80/20 blend. Stearic acid (Pristerene 4981) was obtained from Unichema, and $MgCl_2$ was obtained from J. T. Baker.

For the foaming measurements, a 500 ml, 0.2% active solution of the sample to be tested containing various percentages of SFA per total (SFA and SME) actives was prepared by combining the sample and hard water (with "hard water" containing an approximate 3:2 ratio of calcium to magnesium at 150 ppm) in a flask. The solution was heated to approximately 30° C. and agitated until homogeneous. The solution was then transferred to four 100 mL shake foam cylinders. The four cylinders were sealed and placed in a Gaum 930698 shaking machine. The machine was set to shake to 10 cycles and started once the cylinders were properly placed and locked inside the machine. A reading for each cylinder was taken 15 seconds after the machine shaking cycles were complete. Readings were taken according to the highest point that the foam reached without becoming disattached from the main body of foam. After five minutes an additional reading was taken for each cylinder to determine the stability of thc foam as assessed by foam height in milliliters.

The results of these experiments revealed a surprising result of synergy between the two materials, as displayed by the results presented in Table 3.

TABLE 3

Foam Height for Samples Containing Various Amounts of SFA

| SFA % (SME/SFA ratio) | Initial | 5 minutes |
|---|---|---|
| 4% (22.6/1) | 233 | 230 |
| 12% (7.5/1) | 243 | 243 |
| 25% (3.03/1) | 245 | 243 |
| 40% (1.48/1) | 234 | 229 |
| 56% (1/1.26) | 248 | 248 |
| 71% (1/2.42) | 263 | 263 |
| 86% (1/5.95) | 208 | 205 |

TABLE 3-continued

Foam Height for Samples Containing Various Amounts of SFA

| SFA % (SME/SFA ratio) | Initial | 5 minutes |
|---|---|---|
| 96% (1/22.3) | 180 | 175 |

Namely, as can be seen from Table 3, there surprisingly is no corresponding loss of foam as the SFA content is increased is over a range of from about 4% to about 96%. This indicates that at the lower end of usefulness of the blend is a 1:3 ratio of SME/SFA.

EXAMPLE #8

Characterization of Skin Feel Properties

Skin feel enhancement properties of samples prepared according to the invention were determined using a $C_{16}$-derived 25:1 as compared to 5:1 SME/SFA mixture. The $C_{16}$-derived mixtures were employed instead of MC48-derived mixtures since $C_{,6}$-derived mixtures are a stronger detergent (i.e., harsher on skin) and thus allow a better observation of the 'skin feel effect' described by Farmer and Wells (DE 2403895 Unilever). Therein the inventors refer to the smooth, silky feel left by soap bars containing sulfonated fatty acid, especially sulfonated fatty acids with chain lengths resembling coconut fatty acids, with high lauric and myristic acid contents.

Skin feels tests were conducted using a panel of twenty people using a test procedure in which the subjects were instructed as follows:

1. Wash hands with 1 gram of 15% active ammonium lauryl sulfate solution (ammonium lauryl sulfate from Stepan Company) to remove dirt and sebum from the skin whereby the follow steps are taken:
   (a) washing for 30 seconds
   (b) rinsing for 30 seconds
2. Apply 1 gram of the product in neat form on the palm of the hand two times followed by:
   (a) rubbing with foam generation for 30 seconds
   (b) rinsing for 30 seconds
   (c) repeat again
3. Dry hands with a paper towel and allow to hands to air dry completely.

4. Using a 5 point scale, evaluate the experience based on
   1. Rinsability (1=Bad, 5=Good)
   2. Dryness (1=Bad, 5=Good)
   3. Tightness (1=Bad, 5=Good)
   4. Softness and smoothness (1=not soft and smooth, 5=soft and smooth)
   5. Overall (1=Bad, 5=good, plus any additional comments)
   6. Overall after 15 minutes after drying. (1=Bad, 5=good, plus any additional comments).

The testing results confirm that at a 5:1 ratio of SME to SFA there is a noticeable skin feel enhancement, as compared to a 25:1 ratio of SME to SFA. These results validate that the useful range of SME to SFA ratios are 5:1 and lower, and that SME:SFA ratios of 5:1 and lower are especially useful in producing a finished product with enhanced skin feel characteristics.

EXAMPLE #9

Characterization of Smear and Hardness Properties

The beneficial effect SFA has on smear has been referenced by U.S. Pat. No. 3,247,121, to The Procter and Gamble Company. Compositions of the present invention have the benefit of employing the effect of SFA to compensate for an excessively soluble, sticky, high smearing bar which occurs with higher SME content bars. By virtue of the mere inclusion of SFA, the compositions of the present invention necessarily exhibit improved smear and hardness properties as described in the '121 patent.

EXAMPLE #10

Preferred Dishwashing Paste Blend

This example sets forth a preferred dishwashing paste preparation in accordance with the invention. Initially, a dishwashing past surfactant base is prepared as set forth in Table 4 below:

TABLE 4

Dishwashing Paste Surfactant Base Preparation

| SME/SFA Mix | Dishwash Paste Weight % | Dishwash Paste 1000 Gms |
|---|---|---|
| SME | 0.45 | 450 |
| SFA | 0.15 | 150 |
| $Na_2SO_4$ | 0.023 | 23 |
| UA | 0.029 | 29 |
| TALLIES | | |
| Ratio | | 3.00 |
| % Stearic neutralized | | 78.6% |
| Surfactant Base | | Gms |
| SME/SFA | | 600 |
| Stearic Acid | | 170 |
| Mg $SO_4$ | | 60 |
| NaOH | | 11.2125 |
| $Na_2$ $SO_4$ | | 23 |
| UA | | 29 |

The surfactant base was produced according to the invention. Namely, a methyl ester of composition 60% $C_{12}$, 20% $C_{14}$, 10% $C_{16}$ and 10% $C_{18}$ was sulfonated, treated, and neutralized to produce an aqueous solution containing 45% sulfonated methyl ester, 15% sulfonated fatty acid, and 2.3% sodium sulfate, and 2.9 grams of unreacted methyl ester (UA). Methanol was stripped from the mixture in a vessel capable of good mixing and vacuum. To 1000 grams of this aqueous mixture (i.e., comprising roughly 600 grams of SME/SFA, as indicated in Table 4) was added 170 grams of stearic acid and 60 grams of $MgSO_4$. The mixture was mixed until homogeneous at 90° C. With continued mixing, 39 grams of 50% NaOH solution was added drop wise to convert 80% of the stearic acid to a sodium soap. The resulting 67% solids slurry was then dried on a flaking drum heated to 120° C.

The preferred formulated dishwash paste was produced from the dishwash paste surfactant base as set forth in Table 5.

TABLE 5

Formulated Dishwash Paste
Formula for Dishwashing Paste

| | | Weight % | 1000 Gms |
|---|---|---|---|
| Part A | Surfactant Base | 35.00% | 350 |
| | Ninol LMP | 15.00% | 150 |
| Part B | Zeolite | 20.00% | 200 |
| | $Na_2SO_4$ | 10.00% | 100 |
| | $NaHCO_3$ | 5.00% | 50 |
| Part C | 80/20Soap powder | 5.00% | 50 |
| Part D | Water | 10.00% | 100 |
| Fragrance and Dye | | | 2 |

The paste itself can be produced using a hot pour dishwash paste making procedure. For this procedure, Part A is placed in a vessel capable of good mixing and heating, and melted at a temperature of approximately 90° C. Slowly Part B is added and mixed until homogenous. Once the mixture is fluid, Part C is added. Mixing is continued until homogenous, and Part D is added and again mixed until a homogeneous mixture is obtained. Then fragrance and color are added. The mixture is kept hot and poured into finished containers and allowed to cool and solidify to form a hard paste.

EXAMPLE #11

Preferred Blend for Hot Pour Syndet Toilet Bars

This Example sets forth preferred preparations of the syndet toilet bars in accordance with the invention. The toilet bars can be produced by a variety of means. As described herein, the preferred toiled bar is produced by hot pour.

Initially, for the hot pour syndet toilet bar, a syndet hot pour surfactant base is prepared as set forth in Table 6 below.

TABLE 6

Syndet Hot Pour Toilet Bar Surfactant Base Preparation

| SME/SFA Mix | Syndet Hot Pour Weight % | Syndet Hot Pour 1000 Gms |
|---|---|---|
| SME | 0.49 | 490 |
| SFA | 0.16 | 160 |
| $Na_2SO_4$ | 0.023 | 23 |
| UA | 0.029 | 29 |
| Ratio | | 3.06 |
| % Stearic neutralized | | 32.5% |
| Surfactant Base | | Gms |
| SME/SFA | | 650 |
| Stearic Acid | | 100 |
| Mg $SO_4$ | | 25 |
| NaOH | | 2.73125 |
| $Na_2$ $SO_4$ | | 50.5 |
| UA | | 29 |

The surfactant base was produced according to the invention. Namely, a methyl ester of composition 60% $C_{12}$, 20% $C_{14}$, 10% $C_{16}$ and 10% $C_{18}$ was sulfonated, treated, and neutralized to produce an aqueous solution containing 49% sulfonated methyl ester, 16% sulfonated fatty acid, and 2.3% sodium sulfate, and 2.9 grams of unreacted methyl ester. This mixture (i.e., comprising roughly 650 grams of SME/SFA as set forth in Table 6) was placed in a vessel capable of good heating, mixing, and a vacuum. Methanol was stripped out. To 1000 grams of the aqueous mixture was added: 25 grams of $MgSO_4$, 100 grams of stearic acid, and 27.5 grams of sodium sulfate. The mixture was mixed until homogeneous at 90° C. One third of the stearic acid was then neutralized to sodium stearate by addition of 9.5 grams of 50% NaOH solution and mixed again until homogeneous. The resulting 73% solids slurry was then dried on a flaking drum heated to 130° C. The finished flake is a pale yellow with a melting point of 82° C.

The preferred syndet hot pour toilet bar was produced from the syndet hot pour toilet bar surfactant base as set forth in Table 7.

TABLE 7

Formulated Syndet Hot Pour Toilet Bar
Formula for Syndet Toilet Bar - Hot Pour

| | | Weight % | 1000 Gms |
|---|---|---|---|
| Part A | Surfactant Base | 75.00% | 750 |
| | Stearic Acid | 17.50% | 175 |
| Part B | Water | 3.85% | 38.5 |
| Part C | Coco Fatty Acid | 3.00% | 30 |
| | EDTA | 0.10% | 1 |
| | Fragrance | 0.10% | 1 |
| | BHT | 0.10% | 1 |
| | Citric Acid | 0.15% | 1.5 |
| | Titanium Dioxide | 0.20% | 2 |
| | Dye | 0.01% | 0.1 |

A syndet toilet bar was then produced by placing 750 grams of the flaked surfactant base in a vessel capable of good rnr.xinrg and heating. It was melted and brought to a temperature of about 90–95° C. Approximately 175 grams of stearic acid was slowly added and mixed until homogenous. Once the material was fluid, 38.5 grams of water, Part B, was mixed in followed by a previously blended mixture, Part C, comprising of 30 grams of coco fatty acid, 1.0 gram EDTA, 1.0 gram fragrance, 1.0 gram BHT, 1.5 gram citric acid, 2.0 gram titanium dioxide, and 0.1 gram dye, and mixed until homogenous. Keeping the mixture hot, the liquid was poured into soap molds and allowed to cool and solidify to form a finished toilet bar soap.

EXAMPLE #12

Preferred Blend for Extruded Syndet Toilet Bars

This Example sets forth preferred preparations of the syndet toilet bars in accordance with the invention. The toilet bars can be produced by a variety of means. As described herein, the preferred toiled bar is produced by extrusion.

A preferred extruded syndet toilet bar was prepared by first producing a preferred extruded syndet toilet bar surfactant base, as set forth in Table 8.

TABLE 8

Syndet Extruded Toilet Bar Surfactant Base Preparation

| | Syndet Extruded | |
|---|---|---|
| SME/SFA Mix | Weight % | 1000 Gms |
| SME | 0.325 | 325 |
| SFA | 0.325 | 325 |
| $Na_2SO_4$ | 0.023 | 23 |
| UA | 0.029 | 29 |

TABLE 8-continued

Syndet Extruded Toilet Bar Surfactant Base Preparation

| TALLIES | |
|---|---|
| Ratio | 1.00 |
| % Stearic neutralized | 32.5% |

| Surfactant Base | Gms |
|---|---|
| SME/SFA | 650 |
| Stearic Acid | 100 |
| Mg $SO_4$ | 25 |
| NaOH | 2.73125 |
| $Na_2$ $SO_4$ | 50.5 |
| UA | 29 |

The surfactant base was produced according to the invention. Namely, a methyl ester of composition 60% $C_{12}$, 20% $C_{14}$, 10% $C_{16}$ and 10% $C_{18}$ was sulfonated, treated, and neutralized to produce an aqueous solution containing 32.5% sulfonated methyl ester, 32.5% sulfonated fatty acid, and 2.3% sodium sulfate, and 2.9% of unreacted methyl ester. This mixture (i.e., comprising roughly 650 grams of SME/SFA as set forth in Table 8) was placed in a vessel capable of good heating, mixing, and a vacuum. Methanol was stripped out. To 1000 grams of the aqueous mixture was added finely ground 27.5 grams of sodium sulfate powder, finely ground 25 grams of $MgSO_4$ powder, and 100 grams of stearic acid. The mixture was mixed until homogeneous at 90° C. One third of the stearic acid was then neutralized to sodium stearate by addition of 9.5 grams of 50% NaOH solution and mixed again until homogeneous. The resulting 70% solids slurry was then dried on a flaking drum heated to 130° C. The finished flake is a pale yellow with a melting point of 82° C.

The preferred syndet extruded toilet bar was produced from the extruded toilet bar surfactant base as set forth in Table 9.

TABLE 9

Formulated Syndet Extruded Toilet Bar
Formula for Syndet Toilet Bar - Extruded

| | | Weight % | 1000 Gms |
|---|---|---|---|
| Part A | Surfactant Base | 75.00% | 750 |
| | Stearic Acid | 17.00% | 170 |
| Part B | Water | 4.00% | 40 |
| Part C | Coco Fatty Acid | 3.35% | 33.5 |
| | EDTA | 0.10% | 1 |
| | Fragrance | 0.10% | 1 |
| | BHT | 0.10% | 1 |
| | Citric Acid | 0.15% | 1.5 |
| | Titanium Dioxide | 0.20% | 2 |
| | Dye | 0.01% | 0.1 |

The syndet toilet bar was produced by placing the 750 grams of the flaked surfactant base was placed in a vessel capable of good mixing and heating. It was melted and brought to a temperature of about 90–95° C. Approximately 150 grams of stearic acid was slowly added and mixed until homogenous. Once the material was fluid, 40 grams of water, Part B, was blended in followed by Part C, a previously blended mixture of 33.5 grams of coco fatty acid, 1.0 gram EDTA, 1.0 gram BHT, 1.5 grams citric acid, 2.0 grams titanium dioxide, and 0.1 gram dye, and mixed until homogenous. The mixture was poured onto a cooling belt and fed into a lab scale extruder fitted with a 20 mesh screen in the cone to amalgamate the flakes. The extruder was then fitted with a 50 mesh and the mixture was sent through 4 cycles of plodding. The barrel of the extruder was maintained at 24° C. and the cone at 38° C. Approximately 1 gram of fragrance was added prior to the last plodding cycle. The mixture was extruded into 4 inch billets and cold stamped into finished bars using a small amount of glycerin as a release agent on the surface of the die.

EXAMPLE #13

Preferred Blend for Wet Processed Combo Toilet Bars

This Example sets forth preferred preparations of the combo toilet bars in accordance with the invention. The combo toilet bars can be produced by a variety of means. As described herein, the preferred combo toilet bar is produced by wet processing.

A preferred wet processed combo toilet bar was prepared by first producing a preferred wet processed combo toilet bar surfactant base, as set forth in Table 10.

TABLE 10

Combo Toilet Bar Wet Processing Surfactant Base Preparation

| | Combo Toilet Wet | |
|---|---|---|
| SME/SFA Mix | Weight % | 1000 Gms |
| SME | 0.49 | 490 |
| SFA | 0.16 | 160 |
| $Na_2SO_4$ | 0.023 | 23 |
| UA | 0.029 | 29 |
| TALLIES | | |
| Ratio | | 3.06 |
| % Stearic neutralized | | 66.8% |
| Surfactant Base | | |
| SME/SFA | | 650 |
| Stearic Acid | | 200 |
| Mg $SO_4$ | | 0 |
| NaOH | | 11.2125 |
| $Na_2$ $SO_4$ | | 23 |
| UA | | 29 |
| $MgCl_2$ | | 22.2 |

The surfactant base was produced according to the invention. Namely, a methyl ester of composition 60% $C_{12}$, 20% $C_{14}$, 10% $C_{16}$ and 10% $C_{18}$ was sulfonated, treated, and neutra-lized to produce an aqueous solution containing 49% sulfonated methyl ester, 16 % sulfonated fatty acid, and 2.3% sodium sulfate, and 2.9% of unreacted methyl ester. This mixture (i.e., comprising roughly 650 grams of SME/SFA) was placed in a vessel capable of good heating, mixing, and a vacuum. Methanol was stripped out. To 1000 grams of the aqueous mixture was added 22.2 grams of $MgCl_2$ and followed by 200 grams of stearic acid. The mixture was mixed until homogeneous at 90° C. Two thirds of the stearic acid was then neutralized to sodium stearate by addition of 39.0 grams of 50% NaOH solution and mixed again until homogeneous yielding an 73% solids slurry.

The preferred wet processed combo toilet bar was produced from the combo toilet bar wet processing surfactant base as set forth in Table 11.

TABLE 11

Formulated Syndet Combo Toilet Bar-Wet Processing
Formula for Combo - Wet Processing

| | | Weight % | Gms |
|---|---|---|---|
| Part A | 70% Soap Liquid Base | 75% | 1500 |
| Part B | Wet Process Surfactant | 20% | 350 |
| | Yield of Combo Flakes | | 1305.5 |

TABLE 11-continued

Formulated Syndet Combo Toilet Bar-Wet Processing
Formula for Combo - Wet Processing

| | | Weight % | 1000 Gms |
|---|---|---|---|
| | Combo Flake | | 974 |
| Part C | Coco Fatty Acid | 2.00% | 20 |
| | EDTA | 0.10% | 1 |
| | Fragrance | 0.10% | 1 |
| | BHT | 0.10% | 1 |
| | Citric Acid | 0.15% | 1.5 |
| | Titanium Dioxide | 0.20% | 2 |
| | Dye | 0.01% | 0.1 |

According to Table 11, approximately 1500 grams of Part A (70% active soap liquid base) was prepared using well established continuous or batch soap processing using tallow and coconut fatty acid and sodium hydroxide. Approximately 350 grams of Part B, the aqueous Surfactant Base, was added to the soap solution maintaining a temperature of 95° C. Drying was achieved by heating the mixture to 130° C. using an in line heat exchanger to avoid subjecting the mixture to high heats for extended times. Water was flashed off in a spray chamber and the mixture was collected with a cold screw and extruded into noodles. The resulting noodles (i.e., "combo flakes") were 95% solid with 5% moisture remaining.

Approximately 974 grams of the flakes were amalgamated with Part C which is a pre-blended mixture of 20 grams of coco fatty acid, 1.0 gram EDTA, 1.0 gram BHT, 1.5 grams citric acid, 2.0 grams titanium dioxide, and 0.1 grams dye, by passing through a lab scale extruder fitted with a 20 mesh screen in the cone with a barrel temperature of 24° C. and a cone temperature at 40° C. The mixture was plodded to a homogeneous mixture by passing through the same lab scale extruder fitted with a 50 mesh screen in the cone 4 times. Approximately 1.0 gram of fragrance was added during the last of the plodding cycles. The mixture was extruded into 4 inch billets and cold stamped into finished bars using a small amount of glycerin as a release agent on the surface of the die.

EXAMPLE #14

Preferred Blend for Low Moisture, Dry Processed Combo Toilet Bars

This Example sets forth preferred preparations of the combo toilet bars in accordance with the invention. The combo toilet bars can be produced by a variety of means. As described herein, the preferred combo toilet bar is produced by dry processing, and is a low moisture bar.

A preferred low moisture, dry processed combo toilet bar was prepared by first producing a preferred low moisture, dry processed combo toilet bar surfactant base, as set forth in Table 12.

TABLE 12

Low Moisture Combo Toilet Bar Dry Processing
Surfactant Base Preparation

| | Combo Dry - Toilet | |
|---|---|---|
| SME/SFA Mix | Weight % | 1000 Gms |
| SME | 0.49 | 490 |
| SFA | 0.16 | 160 |
| $Na_2SO_4$ | 0.023 | 23 |
| UA | 0.029 | 29 |

TABLE 12-continued

| Low Moisture Combo Toilet Bar Dry Processing Surfactant Base Preparation | |
|---|---|
| TALLIES | |
| Ratio | 3.06 |
| % Stearic neutralized | 66.8% |
| Surfactant Base | Gms |
| SME/SFA | 650 |
| Stearic Acid | 200 |
| Mg $SO_4$ | 0 |
| NaOH | 11.2125 |
| $Na_2$ $SO_4$ | 23 |
| UA | 29 |
| $MgCl_2$ | 22.2 |

The low moisture, dry processed surfactant base was produced according to the invention. Namely, a methyl ester of composition 60% $C_{12}$, 20% $C_{14}$, 10% $C_{16}$ and 10% $C_{18}$ was sulfonated, treated, and neutralized to produce an aqueous solution containing 49% sulfonated methyl ester, 16% sulfonated fatty acid, and 2.3% sodium sulfate, and 2.9% of unreacted methyl ester. This mixture (i.e., comprising roughly 650 grams of SME/SFA) was placed in a vessel capable of good heating, mixing, and a vacuum. Methanol was stripped out. To 1000 grams of the aqueous mixture was added 22.2 grams of $MgCl_2$ and followed by 200 grams of stearic acid. The mixture was mixed until homogeneous at 90° C. Two thirds of the stearic acid was then neutralized to sodium stearate by addition of 39.0 grams of 50% NaOH solution and mixed again until homogeneous. The slurry was then dried on a flaking drum heated to 130° C. The finished flake is a pale yellow with a melting point of 82° C.

The preferred dry processed low moisture combo toilet bar was produced from the dry processing low moisture surfactant base as set forth in Table 13.

TABLE 13

Formulated Low Moisture Combo Toilet Bar-Dry Processing

| | | | 1000 Gms |
|---|---|---|---|
| Part A | Surfactant Base | 20.00% | 200 |
| | 80/20 Tallow/coco soap | 77.34% | 773.4 |
| Part B | Coco Fatty Acid | 2.00% | 20 |
| | EDTA | 0.10% | 1 |
| | Fragrance | 0.10% | 1 |
| | BHT | 0.10% | 1 |
| | Citric Acid | 0.15% | 1.5 |
| | Titanium Dioxide | 0.20% | 2 |
| | Dye | 0.01% | 0.1 |

For Part A, 773.4 grams of 80/20 tallow/coco soap noodles (92% solid, 8% moisture) and Surfactant Base flakes were amalgamated by passing through a lab scale extruder fitted with a 20 mesh in the cone with a barrel temperature of 24° C. and a cone temperature at 40° C. This mixture was further amalgamated with Part B, which is a pre-blended mixture of 20 grams coco fatty acid, 1.0 gram EDTA, 1.0 grams BHT, 1.5 grams citric acid, 2.0 grams titanium dioxide, and 1.0 gram dye, by passing through a lab scale extruder fitted with a 20 mesh screen in the cone with a barrel temperature of 24° C. and a cone temperature at 40° C. The mixture was plodded to a homogeneous mixture by passing through the same lab scale extruder fitted with a 50 mesh screen in the cone 4 times. Approximately I gram of fragrance was added during the last plodder cycle. The mixture was extruded into 4 inch billets and cold stamped into finished bars using a small amount of glycerin as a release agent on the surface of the die.

EXAMPLE #15

Preferred Blend for High Moisture, Dry Processed Combo Toilet Bars

This Example sets forth preferred preparations of the combo toilet bars in accordance with the invention. The combo toilet bars can be produced by a variety of means. As described herein, the preferred combo toilet bar is produced by dry processing, and is a high moisture bar.

A preferred high moisture, dry processed combo toilet bar was prepared by first producing a preferred high moisture, dry processed combo toilet bar surfactant base, as set forth in Table 14.

TABLE 14

Low Moisture Combo Toilet Bar Dry Processing Surfactant Base Preparation

| | Combo Dry - Toilet | |
|---|---|---|
| SME/SFA Mix | Weight % | 1000 Gms |
| SME | 0.49 | 490 |
| SFA | 0.16 | 160 |
| $Na_2SO_4$ | 0.023 | 23 |
| UA | 0.029 | 29 |
| TALLIES | | |
| Ratio | | 3.06 |
| % Stearic neutralized | | 66.8% |
| Surfactant Base | | Gms |
| SME/SFA | | 650 |
| Stearic Acid | | 200 |
| Mg $SO_4$ | | 0 |
| NaOH | | 11.2125 |
| $Na_2SO_4$ | | 23 |
| UA | | 29 |
| $MgCl_2$ | | 22.2 |

The high moisture, dry processed surfactant base was produced according to the invention. Namely, a methyl ester of composition 60% $C_{12}$, 20% $C_{14}$, 10% $C_{16}$ and 10% $C_{18}$ was sulfonated, treated, and neutralized to produce an aqueous solution containing 32.5% sulfonated methyl ester, 32.5% sulfonated fatty acid, and 2.3% sodium sulfate, and 2.9 % of unreacted methyl ester. This mixture (i.e., comprising roughly 650 grams of SME/SFA) was placed in a vessel capable of good heating, mixing, and a vacuum. Methanol was stripped out. To 1000 grams of the aqueous mixture was added 22.2 grams of $MgCl_2$ and followed by 200 grams of stearic acid. The mixture was mixed until homogeneous at 90° C. Two thirds of the stearic acid was then neutralized to sodium stearate by addition of 39.0 grams of 50% NaOH solution and mixed again until homogeneous. The slurry was then dried on a flaking drum heated to 130° C. The finished flake is a pale yellow with a melting point of 88° C.

The preferred dry processed high moisture combo toilet bar was produced from the dry processing high moisture surfactant base as set forth in Table 15.

TABLE 15

Formulated High Moisture Combo Toilet Bar-Dry Processing

| | | Weight % | 1000 Gms |
|---|---|---|---|
| Part A | Surfactant Base | 20.00% | 200 |
| | 80/20 Tallow/coco soap | 77.34% | 773.4 |
| Part B | Coco Fatty Acid | 2.00% | 20 |
| | EDTA | 0.10% | 1 |
| | Fragrance | 0.10% | 1 |
| | BHT | 0.10% | 1 |
| | Citric Acid | 0.15% | 1.5 |
| | Titanium Dioxide | 0.20% | 2 |
| | Dye | 0.01% | 0.1 |

For Part A, 773.4 grams of 80/20 tallow/coco soap noodles (86% solid, 14% moisture) and Surfactant Base flakes were amalgamated by passing through a lab scale extruder fitted with a 20 mesh in the cone with a barrel temperature of 24° C. and a cone temperature at 40° C. This mixture was further amalgamated with Part B, which is a pre-blended mixture of 20 grams coco fatty acid, 1.0 gram EDTA, 1.0 grams BHT, 1.5 grams citric acid, 2.0 grams titanium dioxide, and 1.0 gram dye, by passing through a lab scale extruder fitted with a 20 mesh screen in the cone with a barrel temperature of 24° C. and a cone temperature at 40° C. The mixture was plodded to a homogeneous mixture by passing through the same lab scale extruder fitted with a 50 mesh screen in the cone 4 times. Approximately I gram of fragrance was added during the last plodder cycle. The mixture was extruded into 4 inch billets and cold stamped into finished bars using a small amount of glycerin as a release agent on the surface of the die.

EXAMPLE 16

Color Stability Studies of Preferred Blends for Combo Bars

Color stability problems were unexpectedly severe when magnesium ion was incorporated into the combo type soap bars using the SME/SFA surfactant base. There is a destructive interaction between magnesium, unsaturated fatty acid soaps and SME/SFA surfactant base. Commonly used preservatives which are employed to solve color stability problems (e.g., BHT, BHA) were ineffective in stopping the problem. Unexpectedly, citric acid (not known as a preservative) was found to disrupt this destructive relationship and prevent the discoloring problem.

Finished bars prepared in accordance with the procedures above and below for the dry process combo toilet bar and the dry process combo laundry bar were compared to a second set of bars prepared using the same formulations with the exception that no citric acid was included. These sets of bars were chosen because the toilet bars are examples of use of magnesium while the laundry bars do not employ magnesium.

One bar of each of the four sets were placed in a oven at 50° C. for up to at least 30 days and color changes were observed over time and compared to a second group serving as a standard which were maintained at room temperature. All bars had the same initial color and appearance.

TABLE 16

Color Changes of Various Formulations of Toilet Bars

| | 7 days | 14 Days | 21 days | 30 days |
|---|---|---|---|---|
| Toilet Combo Bar with citric acid and magnesium ion | No change | No change | No change | No change |
| Toilet Combo Bar without citric acid and with magnesium ion | Slightly Yellow | Yellow | Yellow/Brown | Yellow/Brown |
| Laundry Combo Bar with citric acid and no magnesium ion | No change | No change | No change | No Change |
| Laundry Combo bar without citric acid or magnesium | No change | No change | No Change | No Change |

These results confirm that citric acid can be included in a toilet bar according to the invention to retard bar color changes.

EXAMPLE #17

Preferred Blend for Dry Processed Combo Laundry Bars

This Example sets forth preferred preparations of the combo laundry bars in accordance with the invention. The combo laundry bars can be produced by a variety of means. As described herein, the preferred combo laundry bar is produced by dry processing.

A preferred dry processed combo laundry bar was prepared by first producing a preferred dry processed combo laundry bar surfactant base, as set forth in Table 17.

TABLE 17

Combo Laundry Bar Dy Process Surfactant Base Preparation

| | Combo Dry laundry | |
|---|---|---|
| SME/SFA Mix | Weight % | 1000 Gms |
| SME | 0.52 | 520 |
| SFA | 0.08 | 80 |
| $Na_2SO_4$ | 0.023 | 23 |
| UA | 0.029 | 29 |
| TALLIES | | |
| Ratio | | 6.50 |
| % Stearic neutralized | | 48.9% |
| Surfactant Base | | Gms |
| SME/SFA | | 600 |
| Stearic Acid | | 70 |
| $NaHCO_3$ | | 0 |
| NaOH | | 2.875 |
| $Na_2SO_4$ | | 93 |
| UA | | 29 |
| $MgCl_2$ | | 0 |

The surfactant base was produced according to the invention. Namely, a methyl ester of composition 1% $C_{12}$, 3% $C_{14}$, 96% $C_{16}$ and 1% $C_{18}$ was sulfonated, treated, and neutralized to produce an aqueous solution containing 49% sulfonated methyl ester, 16% sulfonated fatty acid, and 2.3% sodium sulfate, and 2.9% of unreacted methyl ester. This mixture (i.e., comprising roughly 600 grams of SME/SFA as set forth in Table 17) was placed in a vessel capable of good heating, mixing, and a vacuum. Methanol was stripped out. To 1000 grams of the aqueous mixture was added 70 grams of sodium sulfate and followed by 70 grams of stearic acid. The mixture was mixed until homogeneous at 90° C. One half of the stearic acid was then neutralized to sodium stearate by addition of 10 grams of 50% NaOH solution and mixed again until homogeneous. The slurry was then dried on a flaking drum heated to 130° C. The finished flake is a pale yellow with a melting point of 82° C.

The preferred dry processed combo laundry bar was produced from the combo laundry bar dry process surfactant base preparation as set forth in Table 18.

TABLE 18

Formulation for Dry Processed Combo Laundry Base

| | | Weight % | 1000 Gms |
|---|---|---|---|
| Part A | Surfactant Base | 20.00% | 200 |
| | 80/20 Tallow/coco soap | 74.90% | 749 |
| Part B | NaHCO3 | 5% | 50 |
| | Fragrance | 0.10% | 1 |
| | Dye | 0.01% | 0.1 |

As set forth in Table 18, the soap beads and surfactant base flakes are amalgamated by passing through a lab scale extruder fitted with a 20 mesh in the nose with a barrel temperature of 24° C. and a cone temperature at 40° C. This mixture was further amalgamated with Part B which is a pre-blended mixture of $NaHCO_3$, 1.0 grams fragrance, and 0.1 gram dye, by again passing through a lab scale extruder fitted with a 20 mesh screen in the cone with a barrel temperature of 24° C. and a cone temperature at 40° C. The mixture was plodded to a homogeneous mixture by passing through the same lab scale extruder fitted with a 50 mesh screen in the cone 4 times. The mixture was extruded into 4 inch billets and cold stamped into finished bars using a small amount of glycerin as a release agent on the surface of the die.

EXAMPLE #18

Preferred Blend for Wet Processed Combo Laundry Bars

This Example sets forth preferred preparations of the combo laundry bars in accordance with the invention. The combo laundry bars can be produced by a variety of means. As described herein, the preferred combo laundry bar is produced by wet processing.

A preferred wet processed combo laundry bar was prepared by first producing a preferred wet processed combo laundry bar surfactant base, as set forth in Table 19.

TABLE 19

Combo Laundering Bar Wet Processing Surfactant Base Preparation

| | Combo Wet - Laundry | |
|---|---|---|
| SME/SFA Mix | Weight % | 1000 Gms |
| SME | 0.52 | 520 |
| SFA | 0.08 | 80 |
| $Na_2SO_4$ | 0.023 | 23 |
| UA | 0.029 | 29 |
| TALLIES | | |
| Ratio | | 6.50 |
| % Stearic neutralized | | 48.9% |
| Surfactant Base | | Gms |
| SME/SFA | | 600 |
| Stearic Acid | | 70 |
| Mg $SO_4$ | | 0 |
| NaOH | | 2.875 |
| $Na_2SO_4$ | | 93 |
| UA | | 29 |
| $MgCl_2$ | | 0 |

The surfactant base was produced according to the invention. Namely, a methyl ester of composition 1% $C_{12}$, 3% $C_{14}$, 96% $C_{16}$ and 1% $C_{18}$ was sulfonated, treated, and neutralized to produce an aqueous solution containing 49% sulfonated methyl ester, 16% sulfonated fatty acid, and 2.3% sodium sulfate, and 2.9 % of unreacted methyl ester. This mixture (i.e., comprising roughly 600 grams of SME/SFA) was placed in a vessel capable of good heating, mixing, and a vacuum. Methanol was stripped out. To 1000 grams of the aqueous mixture was added 70 grams of sodium sulfate and followed by 70 grams of stearic acid. The mixture was mixed until homogeneous at 90° C. One half of the stearic acid was then neutralized to sodium stearate by addition of 10 grams of 50% NaOH solution and mixed again until homogeneous yielding a 67% solids slurry.

The preferred wet processed combo laundry bar was produced from the combo laundry bar wet processing surfactant base, as set forth in Table 20.

TABLE 20

Formulated Combo Laundry Bar-Wet Processing

| | | | Gms |
|---|---|---|---|
| Part A | 70% Soap Liquid Base | 75% | 1500 |
| Part B | Wet Process Surfactant | 20.2% | 400 |
| | Yield of Combo Flakes | | 1316.095 |
| | | Weight % | 1000 Gms |
| | Combo Flake | | 948.9 |
| Part C | $NaHCO_3$ | 5% | 50 |
| | Fragrance | 0.10% | 1 |
| | Dye | 0.01% | 0.1 |

According to Table 20, approximately 1500 grams of Part A (70% active soap liquid base) was prepared using well established continuous or batch soap processing using tallow and coconut fatty acid and sodium hydroxide. Approximately 400 grams of Part B, the aqueous Surfactant Base, was added to the soap solution maintaining a temperature of 95° C. Drying was achieved by heating the mixture to 130° C. using an in line heat exchanger to avoid subjecting the mixture to the high heats for extended times. Water was flashed off in a spray chamber and the mixture was collected with a cold screw and extruded into noodles. The resulting noodles (i.e., "combo flakes) were 95% solid with 5% moisture remaining.

Approximately 974 grams of the flakes were amalgamated with Part C which is a pre-blended mixture of 50 grams of $NaHCO_3$ and 0.1 grams dye by passing through a lab scale extruder fitted with a 20 mesh screen in the cone with a barrel temperature of 24° C. and a cone temperature at 40° C. The mixture was plodded to a homogeneous mixture by passing through the same lab scale extruder fitted with a 50 mesh screen in the cone 4 times. 1.0 grams of fragrance was added during the last of the plodding cycles. The mixture was extruded into 4 inch billets and cold stamped into finished bars using a small amount of glycerin as a release agent on the surface of the die.

EXAMPLE #19

Preferred Blend for Extruded Syndet Laundry Bars

This Example sets forth preferred preparations of the syndet laundry bars in accordance with the invention. The syndet laundry bars can be produced by a variety of means. As described herein, the preferred syndet laundry bar is produced by extrusion.

A preferred extruded syndet laundry bar was prepared by first producing a preferred extruded syndet laundry bar surfactant base, as set forth in Table 21.

TABLE 21

Extruded Syndet Laundry Bar Surfactant Bar Preparation

| | Syndet laundry | |
|---|---|---|
| SME/SFA Mix | Weight % | 1000 Gms |
| SME | 0.52 | 520 |
| SFA | 0.08 | 80 |
| $Na_2SO_4$ | 0.023 | 23 |
| UA | 0.029 | 29 |
| TALLIES | | |
| Ratio | | 6.50 |
| % Stearic neutralized | | 48.9% |
| Surfactant Base | | Gms |
| SME/SFA | | 600 |
| Stearic Acid | | 70 |
| Mg $SO_4$ | | 0 |
| NaOH | | 2.875 |
| $Na_2SO_4$ | | 93 |
| UA | | 29 |
| $MgCl_2$ | | 0 |

The extruded syndet laundry bar surfactant base was produced according to the invention. Namely, a methyl ester of composition 1% $C_{12}$, 3% $C_{14}$, 96% $C_{16}$ and 1% $C_{18}$ was sulfonated, treated, and neutralized to produce an aqueous solution containing 52% sulfonated methyl ester, 8% sulfonated fatty acid, and 2.3% sodium sulfate, and 2.9 grams of unreacted methyl ester. This mixture (i.e., comprising roughly 600 grams of SME/SFA) was placed in a vessel capable of good heating, mixing, and a vacuum. Methanol was stripped out. To 1000 grams of the aqueous mixture was added 35 grams of stearic acid and 35 grams of finely ground sodium sulfate powder. The mixture was mixed until homogeneous at 90° C. One half of the stearic acid was then neutralized to sodium stearate by addition of 5 grams of 50% NaOH solution and mixed again until homogeneous. The slurry was then dried on a flaking drum heated to 130° C. The finished flake is a pale yellow with a melting point of 82° C.

The preferred extruded syndet laundry bar was produced from the extruded syndet laundry bar surfactant base as set forth in Table 22.

TABLE 22

Formulated Extruded Syndet Laundry Bar

| | | Weight % | 1000 Gms |
|---|---|---|---|
| Part A | Surfactant Base | 35.00% | 350 |
| Part B | Zeolite | 20.00% | 200 |
| | Na2SO4 | 20.00% | 200 |
| | NaHCO3 | 5.00% | 50 |
| Part C | Water | 5.00% | 50 |
| Fragrance and Dye | | | 2 |

Namely, Part A, 350 grams of the surfactant base flake above, was amalgamated along with Part B, 200 grams of Aluminosilicate, 350 grams of $Na_2SO_4$, and 50 grams of $NaHCO_3$, by feeding into a lab scale extruder fitted with a 20 mesh screen in the cone with a barrel temperature of 24° C. and a cone temperature at 40° C. When homogeneous, Part C, 50 grams of water, was added and again passed through the amalgamator. The blend was then amalgamated again with 0.1 gram dye. The lab extruder was then fitted with a 50 mesh screen in the cone and the mixture was sent through 4 cycles of plodding. The barrel of the extruder was maintained at 24° C. and the cone at 38° C. 1.0 grams of fragrance was plodded into the mixture during the last plodding cycle. The mixture was extruded into 4 inch billets and cold stamped into finished bars using a small amount of glycerin as a release agent on the surface of the die.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A composition suitable for formation into mild personal cleansing or laundry detergent bars comprising:

(a) from about 50% to about 90% by weight of a mixture of an anionic surfactants comprising i) an alpha sulfonated alkyl ester of the formula

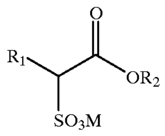

wherein $R_1$ is $C_{10}$–$C_{18}$ alkyl, $R_2$ is a straight or branched chain $C_1$–$C_6$ alkyl, and M is hydrogen or sodium, potassium, calcium, magnesium, monoethanolammonium, diethanolammonium, triethanolammonium, or a mixture thereof; and ii) a sulfonated fatty acid of the formula

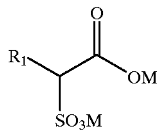

wherein $R_1$ is a $C_{10}$–$C_{18}$ alkyl, and each M is independently hydrogen and/or sodium, potassium, calcium, magnesium, monoethanolammonium, diethanolammonium, triethanolammonium, or a mixture thereof;

(b) from about 10% to about 50% by weight of a fatty acid of the formula

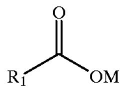

wherein $R_1$ is a $C_{16}$–$C_{18}$ alkyl, and M is hydrogen and/or sodium, potassium, calcium, magnesium, monoethanolammonium, diethanolammonium, triethanolammonium, or a mixture thereof; and (c) from about 0.1% to about 20% by weight water;

wherein the ratio of i) to ii) is from about 8:1 to about 1:2; and wherein the ratio of (a) to (b) is about 9:1 to about 1:1.

2. A composition according to claim 1, further comprising from about 0.1% to about 10% by weight of an alkali metal inorganic salt selected from the group consisting of sodium sulfate, sodium chloride, sodium carbonate, potassium sulfate, potassium chloride, potassium carbonate, calcium sulfate, calcium chloride, calcium carbonate, magnesium sulfate, magnesium chloride, or magnesium carbonate, or mixtures thereof.

3. A composition according to claim 1, further comprising from about 1% to about 15% by weight paraffin.

4. A composition according to claim 1, wherein the alpha sulfonated alkyl ester is a sulfonated methyl ester.

5. A composition according to claim 1, wherein the alpha sulfonated alkyl ester is of the formula

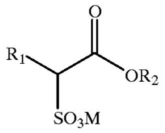

wherein $R_1$ is about 80% $C_{12}$–$C_{15}$ alkyl, and about 20% of a mixture of $C_8$–$C_{10}$ and $C_{16}$–$C_{18}$ alkyl; wherein $R_2$ methyl, and M is hydrogen or sodium, potassium, calcium, or magnesium, or a mixture thereof.

6. A composition according to claim 1, wherein the sulfonated fatty acid is of the formula

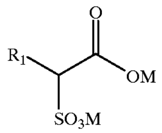

wherein $R_1$ is at least 80% $C_{14}$–$C_{16}$ alkyl, and about 0–20% of a mixture of $C_{10}$–$C_{13}$ and $C_{17}$–$C_{18}$ alkyl; and wherein M is hydrogen and/or sodium, potassium, calcium, magnesium, or a mixture thereof.

7. A composition according to claim 1, wherein the composition exists as solid flakes.

8. A transparent mild personal cleansing or laundry detergent bar comprising a composition according to claim 1.

9. A composition according to claim 1, further comprising about 0.5% to about 10% by weight of a sucrogylceride, a functional metallic soap, a succinamate, a sulfosuccinamate, a mono-, di-, or trigylceride, chitosan, or a mixture thereof.

10. A composition suitable for formation into mild personal cleansing or laundry detergent bars comprising:

(a) from about 60% to about 80% by weight of a mixture of an anionic surfactants comprising i) an alpha sulfonated alkyl ester of the formula

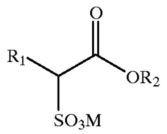

wherein $R_1$ is at least 80% $C_{12}$–$C_{15}$ alkyl, and about 0–20% of a mixture of $C_8$–$C_{10}$ and $C_{16}$–$C_{18}$ alkyl, wherein $R_2$ is methyl, and M is hydrogen or sodium, potassium, calcium, magnesium, or a mixture thereof; and ii) a sulfonated fatty acid of the formula

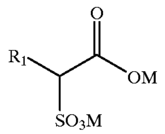

wherein $R_1$ is about 80% $C_{12}$–$C_{15}$ alkyl, and about 20% of a mixture of $C_8$–$C_{10}$ and $C_{16}$–$C_{18}$ alkyl; and each M is independently hydrogen and/or sodium, potassium, calcium, magnesium, or a mixture thereof;

(b) from about 20% to about 30% by weight of a fatty acid of the formula

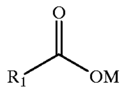

wherein $R_1$ is a $C_{16}$–$C_{18}$ alkyl, or combination thereof, and M is hydrogen and/or sodium, potassium, calcium, magnesium, or a mixture thereof; and (c) an amount of water sufficient to provide a melting point of the composition of between 60° C. and 80° C.;

wherein the ratio of i) to ii) is from about 7:1 to about 1:2; and wherein the ratio of (a) to (b) is about 4:1 to about 3:2.

* * * * *